US008265357B2

(12) United States Patent
Ramsing et al.

(10) Patent No.: US 8,265,357 B2
(45) Date of Patent: Sep. 11, 2012

(54) DETERMINATION OF A CHANGE IN A CELL POPULATION

(75) Inventors: Niels B. Ramsing, Risskov (DK); Jorgen Berntsen, Viborg (DK)

(73) Assignee: Unisense FertiliTech A/S, Aarhus N (DK)

( * ) Notice: Subject to any disclaimer, the term of this patent is extended or adjusted under 35 U.S.C. 154(b) by 1112 days.

(21) Appl. No.: 12/090,110

(22) PCT Filed: Oct. 16, 2006

(86) PCT No.: PCT/DK2006/000581
§ 371 (c)(1),
(2), (4) Date: Jun. 16, 2008

(87) PCT Pub. No.: WO2007/042044
PCT Pub. Date: Apr. 19, 2007

(65) Prior Publication Data
US 2008/0247628 A1   Oct. 9, 2008

Related U.S. Application Data

(60) Provisional application No. 60/726,795, filed on Oct. 14, 2005, provisional application No. 60/814,115, filed on Jun. 16, 2006.

(30) Foreign Application Priority Data

Oct. 14, 2005   (DK) ................................. 2005 01438
Jun. 16, 2006   (DK) ................................. 2006 00821

(51) Int. Cl.
*G06K 9/00*       (2006.01)
*A61B 6/00*       (2006.01)

(52) U.S. Cl. ............................ 382/128; 356/39; 345/587
(58) Field of Classification Search ....................... None
See application file for complete search history.

(56) References Cited

U.S. PATENT DOCUMENTS 3,618,734 A    11/1971   Khan
(Continued)

FOREIGN PATENT DOCUMENTS

DE    100 17 192 A1    10/2001
(Continued)

OTHER PUBLICATIONS

Hnida Christina et al: Computer-controlled, multilevel, morphometric analysis of blastomere size as biomarker of fragmentation and multinuclearity in human embryos. Human Reproduction, vol. 19, No. 2, Feb. 2004, pp. 288-293.

(Continued)

*Primary Examiner* — Jermele M Hollington
*Assistant Examiner* — Trung Nguyen
(74) *Attorney, Agent, or Firm* — Gifford, Krass, Sprinkle, Anderson & Citkowski, P.C.

(57) ABSTRACT

The present invention relates to a method and a system for determination of a change in a cell population, as well as a method for using said method and system for estimating a quality measure of embryos and for selecting embryos for in vitro fertilization, said method comprising the steps of sequentially acquiring at least two images of the cell population, comparing at least a part of the at least two images obtaining at least one difference image, computing a parameter from the at least one difference image, based on said computed parameter determining whether a change has occurred.

49 Claims, 16 Drawing Sheets

U.S. PATENT DOCUMENTS

| | | | |
|---|---|---|---|
| 4,649,114 | A | 3/1987 | Miltenberger et al. |
| 4,724,543 | A | 2/1988 | Klevecz et al. |
| 4,894,343 | A | 1/1990 | Tanaka et al. |
| 4,895,805 | A | 1/1990 | Sato et al. |
| 5,196,168 | A | 3/1993 | Muszak et al. |
| 5,652,142 | A | 7/1997 | Barker et al. |
| 5,763,279 | A | 6/1998 | Schwarz et al. |
| 5,968,340 | A | 10/1999 | Land et al. |
| 6,228,636 | B1 | 5/2001 | Yahiro et al. |
| 6,391,577 | B1 | 5/2002 | Mikkelsen et al. |
| 6,434,320 | B1 | 8/2002 | Myers |
| 6,730,471 | B1 | 5/2004 | Katerkamp et al. |
| 7,336,401 | B2 * | 2/2008 | Unal et al. ............... 358/448 |
| 7,724,937 | B2 * | 5/2010 | So et al. .................. 382/133 |
| 2002/0072113 | A1 | 6/2002 | Barbera-Guillem et al. |
| 2003/0138942 | A1 | 7/2003 | Cecchi et al. |
| 2003/0185450 | A1 | 10/2003 | Garakani et al. |
| 2004/0147012 | A1 | 7/2004 | Yokoi et al. |
| 2004/0180428 | A1 | 9/2004 | Takeshita et al. |
| 2005/0041102 | A1 | 2/2005 | Bongiovanni et al. |
| 2005/0205673 | A1 | 9/2005 | Morris et al. |

FOREIGN PATENT DOCUMENTS

| | | |
|---|---|---|
| DK | 2005 01438 | 4/2007 |
| EP | 0 311 059 | 4/1989 |
| EP | 0 448 923 | 11/1990 |
| EP | 1 041 154 | 12/1995 |
| EP | 1 134 583 | 3/2000 |
| EP | 1 531 422 | 5/2005 |
| EP | 1542154 | 6/2005 |
| EP | 1 595 941 | 11/2005 |
| EP | 1 916 296 | 4/2008 |
| GB | 1 426 786 | 9/1973 |
| JP | 2001-330582 | 11/2001 |
| JP | 2002-122568 | 4/2002 |
| JP | 2005/168341 | 6/2005 |
| JP | 2006014675 | 1/2006 |
| JP | 2006/034256 | 2/2006 |
| RU | 2187111 | 8/2002 |
| WO | WO 87/05114 | 8/1987 |
| WO | WO 91/06628 | 5/1991 |
| WO | WO 92/20359 | 11/1992 |
| WO | WO 97/19345 | 5/1997 |
| WO | WO 98/05753 | 2/1998 |
| WO | WO-9821309 A1 | 5/1998 |
| WO | WO 00/44876 | 8/2000 |
| WO | WO 00/58437 | 10/2000 |
| WO | WO 01/02539 | 1/2001 |
| WO | WO 01/02598 | 1/2001 |
| WO | WO 01/23886 | 4/2001 |
| WO | WO 01/26609 | 4/2001 |
| WO | WO 03/077552 | 9/2003 |
| WO | WO 2004/056265 | 7/2004 |
| WO | WO 2005/039181 | 4/2005 |
| WO | WO 2007/042044 | 4/2007 |
| WO | WO 2007/144001 | 12/2007 |
| WO | WO 2007/145196 | 12/2007 |
| WO | WO 2007/145198 | 12/2007 |
| WO | WO 2009/003487 | 1/2009 |

OTHER PUBLICATIONS

Beliën et al., 1997, "Counting mitoses by image processing in feulgen stained breast cancer sections: The influence of resolution". Cytometry 28, pp. 135-140.

Bhattacharya et al., 2004, "What is the most relevant standard of success in assisted reproduction? Redefining success in the context of elective single embryo transfer: evidence, intuition and financial reality", Human reproduction pp. 1-4.

Biran et al: "Optical imaging fiber-based single live cell arrays: a high density cell assay platform", Anal. Chem. 2002, vol. 74, pp. 3046-3054.

Bos-Mikich et al., 2001, "Early cleavage of human embryos: an effective method for predicting successful IVF/ICSI outcome", Hum Reprod 16, pp. 2658-2661.

Curl et al., 2004, "Quantitative phase microscopy: a new tool for measurement of cell culture growth and confluency in situ". Pflugers Arch—Eur J Physiol 448, pp. 462-468.

Eccles et al., 1986, "Automatic digital image analysis for identification of mitotic cells in synchronous mammalian cell cultures". Pubmed, anal quant cytol histol 8: pp. 138-147.

Eshre position paper on the EU Tissues and Cells Directive EC/2004/23, Nov. 2007.

Fenwick et al., 2002, "Time from insemination to first cleavage predicts developmental competence of human preimplantation embryos in vitro", Hum reprod 17, pp. 407-412.

Gonzales et.al., 1995, "Prediction of the development potential of hamster embryos in vitro by precise timing of the third cell cycle", Journal of Reproduction and Fertility, vol. 105, No. 1, pp. 1-8.

Grenier Microplate Dimensions Guide (2007), Compendium of Greiner Bio-One Microplates.

Grisart et.al., 1994, "Cinematographic analysis of bovine embryo development in serum-free oviduct-conditioned medium", Journal of Reproduction and Fertility, vol. 101, No. 2, pp. 257-264.

Haney et al., 2001, "Tracking tumor growth rates in Patients with Malignant gliomas: A test of two algorithms". AJNR An J Neuroradiol 22, pp. 73-82.

Holm et al., 2002, "Kinetics of early in vitro development of bovine in vivo-and in vitro-derived zygotes produced and/or cultured in chemically defined or serum-containing media", Reproduction 123, pp. 553-565.

Holm et al., 2003 "Developmental kinetics of bovine nuclear transfer and parthenogenetic embryos", Cloning and stem cell, vol. 5 No. 2, pp. 133-142.

Holm et.al., 1998, "Development kinetics of the first cell cycles of bovine in vitro produced embryos in relation to their in vitro viablity and sex", Theriogenology, vol. 50, No. 8, pp. 1285-1299.

Houghton et al., 1996, "Oxygen Consumption and Energy Metabolism of the Early Mouse Embryo", Molecular reproduction and development 44, pp. 476-485.

Jung et al., "Oxygen microsensor and its application to single cells and mouse pancreatic islets", Anal. Chem., 1999, 71, 3642-3649.

Lane et al: "Selection of viable mouse blastocysts prior to transfer using a metabolic criterion", Human Reproduction vol. 11, No. 9, pp. 1975-1978, 1996.

Lequarre et.al., 2003, "Cell cycle duration at the time of maternal zygotic transition for in vitro produced bovine embryos: Effect of oxygen tension and transcription inhibition", Biology of Reproduction, vol. 69, No. 5, pp. 1707-1713.

Lundin et al., 2001, "Early embryo cleavage is a strong indicator of embryo quality in human IVF", Human Reproduction, vol. 16, No. 12, pp. 2652-2657.

Magnusson et al., 1986, "Oxygen consumption by human oocytes and blastocysts grown in vitro", Human Reproduction vol. 1 No. 3 pp. 183-184.

Majerus et al., 2000, "Characterization of embryos derived from calf oocytes: Kinetics of cleavage, cell allocation to Inner cell mass, and trophectoderm and lipid metabolism", Molecular reproduction and development 57, pp. 346-352.

Motosugi et al., 2005, "Polarity of the mouse embryo is established at blastocyst and is not prepatterned", Genes & development 19, pp. 1081-1092.

Neuber et al., 2003, "Sequential assessment of individually cultured human embryos as an indicator of subsequent good quality blastocyst development", Human Reprod vol. 18, pp. 1307-1312.

Oberholzer et al., 1996, "Methods in quantitative image analysis". Histochem Cell Boil 105, pp. 333-355.

Overstrom, Eric W., 1996, "In vitro assessment of embryo viability", Theriogenology, vol. 45, pp. 3-16.

Petersen et al., 2001, "Embryo selection by the first cleavage parameter between 25 and 27 hours after ICS" I. J Assist Reprod Genet 18, vol. 4, pp. 209-212.

Sakkas et al., 1998, "Early cleavage of human embryos to the two-cell stage after intracytoplasmic sperm injection as an indicator of embryo viability", Hum Reprod 13, pp. 182-187.

Sakkas et al., 2001, "Assessment of early cleaving in vitro fertilized human embryos at the 2-cell stage before transfer improves embryo selection", Fertil Steril 76, pp. 1150-1156.

Salumets et al., 2002, "The predictive value of pronuclear morphology of zygotes in the assessment of human embryo quality", Hum Reprod 16, pp. 2177-2181.

Schatten et.al., 2005, "The significance of mitochondria for embryo development in cloned farm animals", Mitochondrion, Elsevier, Amsterdam, NL, vol. 5, No. 5, pp. 303-321.

Shiku et al., 2001, "Oxygen Consumption of Single Bovine Embryos Probed by Scanning Electrochemical Microscopy", Anal. Chem., 73, pp. 3751-3758.

Shoukir et al., 1997, "Early cleavage of in-vitro fertilized embryos to the 2-cell stage: a novel indicator of embryo quality and viability". Hum Reprod 12, pp. 1531-1536.

Squirrell et.al., 1999, "Long-term two-photon fluorescence imaging of mammalian embryos without compromising viability", Nature Biotechnology, Nature Publishing Group, vol. 11, No. 17, pp. 763-767.

Squirrell et.al., 2003, "Imaging mitochondrial organization in living primate oocytes and embryos using multiphoton microscopy", Microscopy and Microanalysis, Springer, New York, vol. 9, No. 3. pp. 190-201.

Tokura et.al., 1993, "Sequential observation of mitochondrial distribution in mouse oocytes and embryos", Journal of Assisted Reproduction and Genetics, vol. 10, No. 6, pp. 417-426.

Trettnak et al., 1998, "Optical oxygen sensor instrumentation based on the detection of luminescence lifetime", Adv. Space Res. vol. 22, No. 10, pp. 1465-1474.

Trimarchi et al., "Oxidative phosphorylation-dependent and -independent oxygen consumption by individual preimplantation mouse embryos", Biol. Reprod., 62, 1866-1874, 2000.

Van Blerkom et.al., 2001, "A microscopic and biochemical study of fragmentation phenotypes in stage-appropriate human embryos", Human Reproduction, vol. 16, No. 4, pp. 719-729.

Vayena et al., 2001, "Current practices and controversies in assisted reproduction": Report of a meeting on "Medical, Ethical and Social aspects of assisted reproduction" held at WHO headquarters in Geneva, Switzerland.

Windt et al., 2004, "Comparative analysis of pregnancy rates after the transfer of early dividing embryos versus slower dividing embryos", Hum Reprod vol. 19 No. 5 pp. 1155-1162.

Wodnicka et al., "Novel fluorescent technology platform for high throughput cytotoxicity and proliferation assays", Jour. Biomol. screening, 5, 3, 141-152, 2000.

Wong et al., 2002, "Non-invasive imaging of human embryos before embryonic genome activation predicts development to the blastocyst stage", Nature Biotechnology, vol. 28, No. 10, pp. 1115-1124.

\* cited by examiner

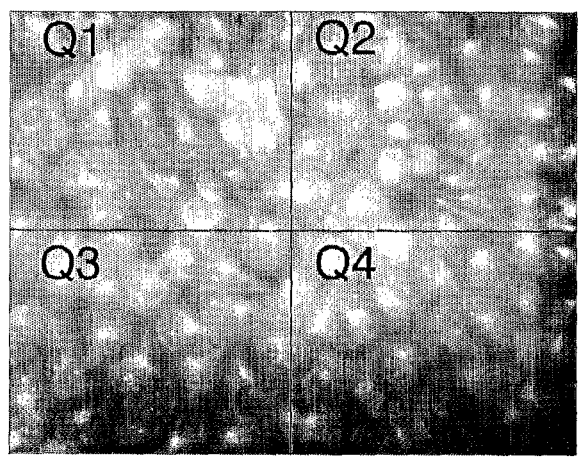
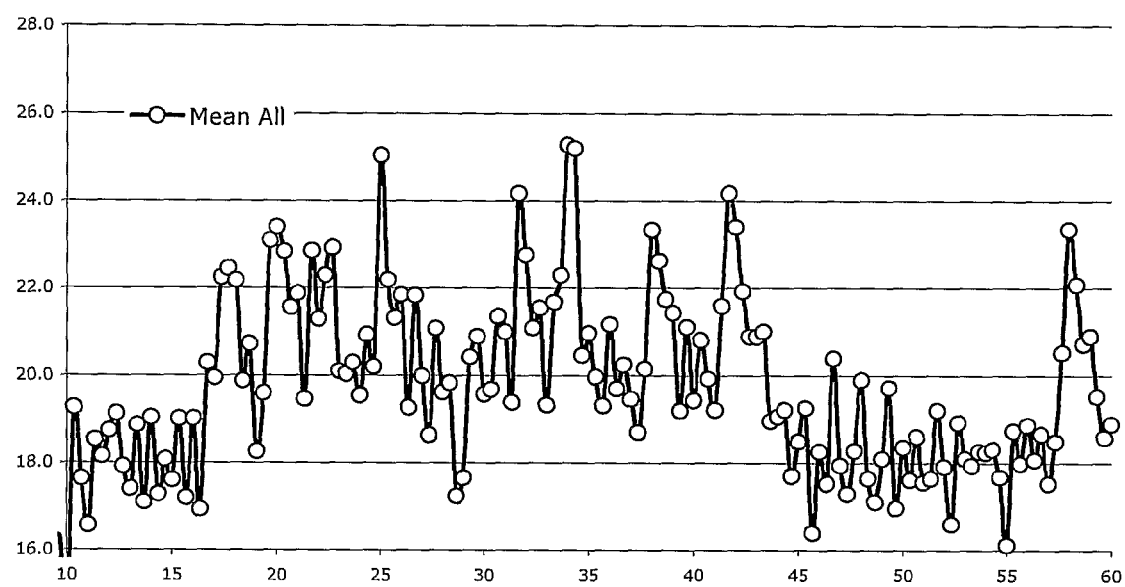
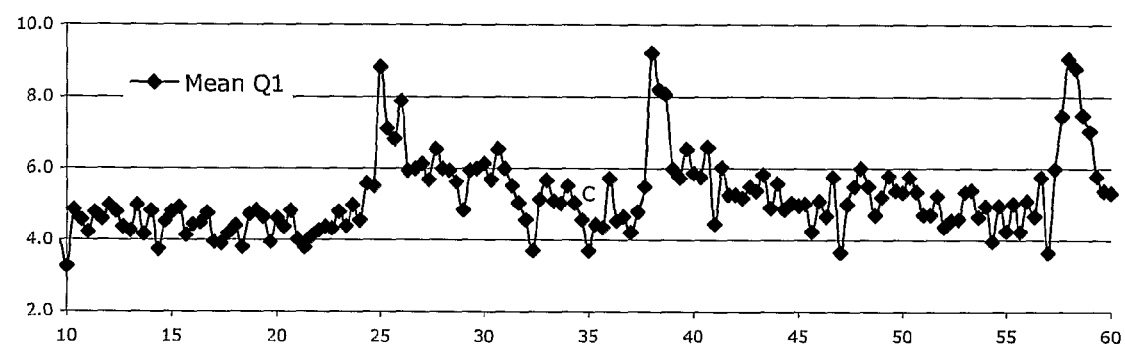
Fig. 6

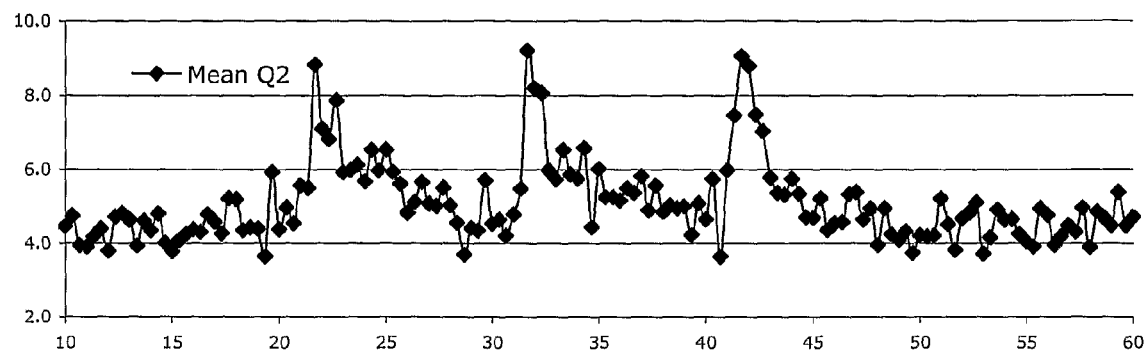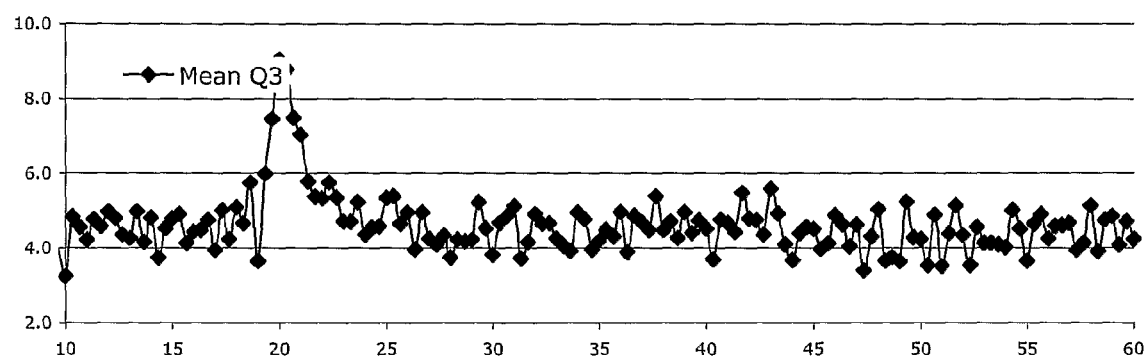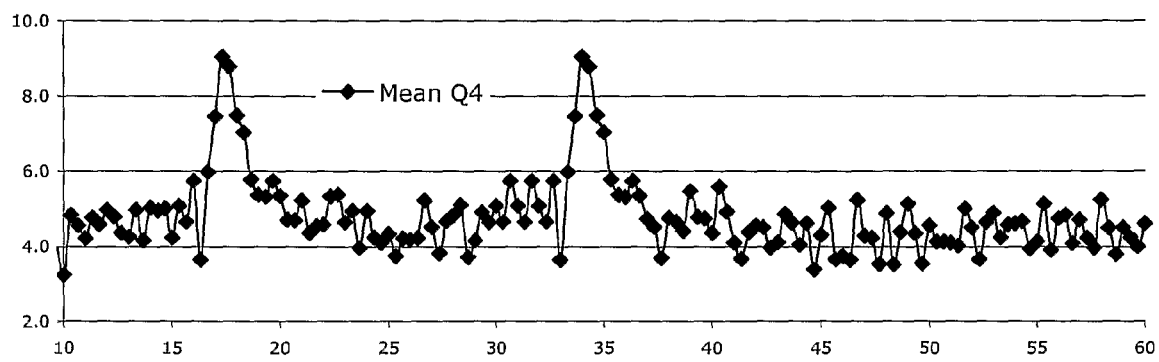
Fig. 6 (continued)

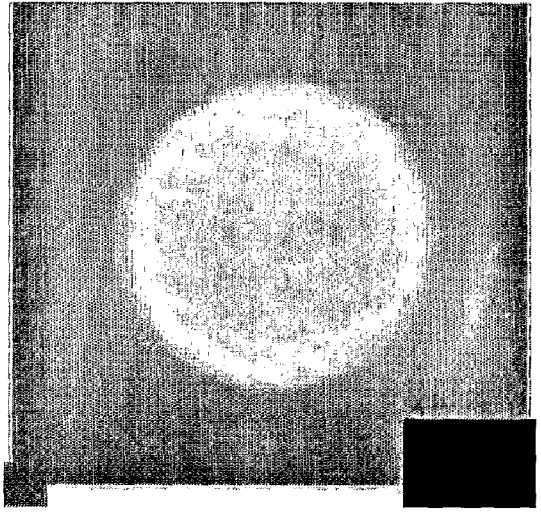 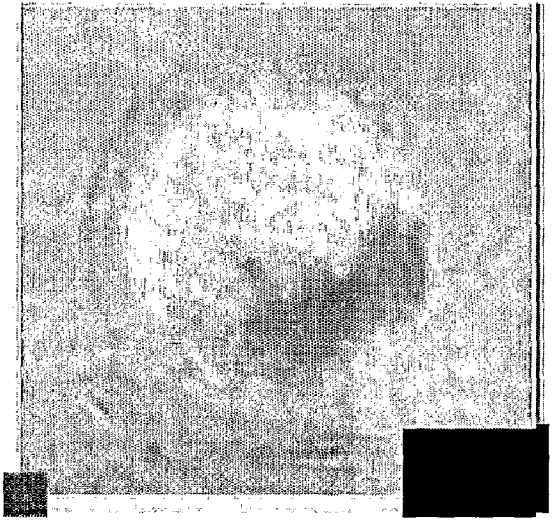
Fig. 10

Embryo selection based on ratios of average and of standard deviation for blastomere activity in different segments

Bad embryos

| Sections | | Time (h) | | Frame | | | Time (t Frame | | | | Time (t Frame | | |
|---|---|---|---|---|---|---|---|---|---|---|---|---|---|
| | | Part 1 | 32 | 73 | | Part 2 | 60 | 129 | | Part 3 | 75 | 159 | |
| | | | 60 | 129 | | | 75 | 159 | | | 96 | 201 | |

| Criteria 1 | | | | | | | | | | | | | | | | | | | |
|---|---|---|---|---|---|---|---|---|---|---|---|---|---|---|---|---|---|---|---|
| | Average Part 1 | 16.2 | 17.0 | 12.7 | 15.3 | 14.7 | 17.6 | 21.7 | 16.7 | 17.4 | 15.8 | 16.2 | 19.3 | 15.4 | 18.9 | 12.9 | 15.4 | 15.4 | 16.6 | 16.2 | 13.8 | 20.1 |
| | Average Part 3 | 13.8 | 15.5 | 8.8 | 14.4 | 14.4 | 14.9 | 15.9 | 13.7 | 14.6 | 11.3 | 12.3 | 14.3 | 12.8 | 13.5 | 10.9 | 12.0 | 12.2 | 8.5 | 13.9 | 10.5 | 15.6 |
| | Ratio < | 1.17 | 1.09 | 1.44 | 1.07 | 1.02 | 1.18 | 1.37 | 1.22 | 1.19 | 1.41 | 1.32 | 1.35 | 1.20 | 1.40 | 1.18 | 1.28 | 1.25 | 1.96 | 1.17 | 1.31 | 1.21 |

| Criteria 2 | | | | | | | | | | | | | | | | | | | |
|---|---|---|---|---|---|---|---|---|---|---|---|---|---|---|---|---|---|---|---|
| | StDev Part 2 | 0.655 | 0.709 | 1.473 | 0.628 | 0.425 | 1.405 | 0.579 | 0.752 | 0.693 | 0.99 | 1.934 | 1.582 | 1.06 | 0.495 | 0.737 | 0.498 | 0.489 | 1.364 | 0.671 | 3.352 | 0.898 |
| | StDev Part 3 | 3.138 | 0.983 | 1.584 | 1.094 | 1.377 | 1.206 | 2.917 | 1.157 | 0.944 | 1.977 | 1.354 | 2.092 | 1.086 | 0.581 | 0.605 | 1.644 | 1.703 | 2.029 | 2.319 | 4.546 | 1.05 |
| | Ratio < | 0.209 | 0.721 | 0.930 | 0.574 | 0.309 | 1.165 | 0.198 | 0.650 | 0.734 | 0.500 | 1.429 | 0.756 | 0.976 | 0.852 | 1.219 | 0.303 | 0.287 | 0.672 | 0.289 | 0.737 | 0.855 |

Combined

Good embryos

| Criteria 1 | | | | | | | | | | | | | | | | | | | |
|---|---|---|---|---|---|---|---|---|---|---|---|---|---|---|---|---|---|---|---|
| | Average Part 1 | 15.6 | 15.2 | 15.3 | 15.9 | 17.4 | 15.8 | 16.0 | 16.1 | 16.0 | 15.6 | 17.1 | 14.7 | 15.6 | 19.7 | 19.7 | 15.8 | 15.2 | 16.6 | | | |
| | Average Part 3 | 16.3 | 15.9 | 15.8 | 15.9 | 17.3 | 15.1 | 14.8 | 16.6 | 14.0 | 15.6 | 14.0 | 15.0 | 12.1 | 17.9 | 17.8 | 15.3 | 15.0 | 14.8 | | | |
| | Ratio < | 0.96 | 0.95 | 0.97 | 1.00 | 1.01 | 1.05 | 1.08 | 0.97 | 1.14 | 1.00 | 1.22 | 0.98 | 1.29 | 1.10 | 1.11 | 1.03 | 1.02 | 1.12 | | | |

| Criteria 2 | | | | | | | | | | | | | | | | | | | |
|---|---|---|---|---|---|---|---|---|---|---|---|---|---|---|---|---|---|---|---|
| | StDev Part 2 | 0.909 | 0.519 | 0.444 | 0.524 | 0.632 | 0.75 | 0.518 | 0.581 | 0.699 | 0.703 | 0.92 | 0.79 | 0.413 | 0.888 | 0.909 | 0.551 | 0.504 | 0.473 | | | |
| | StDev Part 3 | 1.824 | 2.347 | 2.211 | 1.544 | 2.88 | 2.25 | 1.328 | 2.662 | 1.433 | 1.536 | 2.045 | 2.558 | 0.677 | 2.103 | 3.043 | 2.075 | 1.671 | 1.71 | | | |
| | Ratio < | 0.498 | 0.221 | 0.201 | 0.339 | 0.219 | 0.333 | 0.390 | 0.218 | 0.488 | 0.458 | 0.450 | 0.309 | 0.609 | 0.422 | 0.299 | 0.265 | 0.302 | 0.277 | | | |

Combined

Fig. 13

DETERMINATION OF A CHANGE IN A CELL POPULATION

CROSS-REFERENCE TO RELATED APPLICATIONS

This application is the U.S. National Phase of PCT/DK2006/000581 filed Oct. 16, 2006, which claims priority of Danish Patent Application PA 2005 01438 filed Oct. 14, 2005; U.S. Provisional Patent Application 60/726,795 filed Oct. 14, 2005; Danish Patent Application PA 2006 00821 filed Jun. 16, 2006; and U.S. Provisional Patent Application 60/814,115 filed Jun. 16, 2006.

FIELD OF THE INVENTION

The present invention relates to a method and a system for determination of a change in a cell population, as well as a method for using said method and system for estimating a quality measure of embryos and for selecting embryos for in vitro fertilisation.

BACKGROUND

Infertility affects more than 80 million people worldwide. It is estimated that 10% of all couples experience primary or secondary infertility (Vayena et al. 2001). In vitro fertilization (IVF) is an elective medical treatment that may provide a couple who has been otherwise unable to conceive a chance to establish a pregnancy. It is a process in which eggs (oocytes) are taken from a woman's ovaries and then fertilized with sperm in the laboratory. The embryos created in this process are then placed into the uterus for potential implantation. To avoid multiple pregnancies and multiple births only a few embryos are transferred (normally less than four and ideally only one (Bhattacharya et al. 2004)). Selecting proper embryos for transfer is a critical step in any IVF-treatment. Current selection procedures are mostly entirely based on morphological evaluation of the embryo at different timepoints during development and particularly an evaluation at the time of transfer using a standard stereomicroscope. However, it is widely recognized that the evaluation procedure needs qualitative as well as quantitative improvements.

Early cell division. A promising new approach is to use 'early division' to the 2-cell stage, (i.e. before 25-27 h post insemination/injection), as a quality indicator. In this approach the embryos are visually inspected 25-27 hours after fertilization to determine if the first cell division has been completed. Several studies have demonstrated strong correlation between early cleavage and subsequent development potential of individual embryos. (Shoukir et al., 1997; Sakkas et al., 1998, 2001; Bos-Mikich et al., 2001; Lundin et al., 2001; Petersen et al., 2001; Fenwick et al., 2002; Neuber et al. 2003; Salumets et al., 2003; Windt et al., 2004). The need for more frequent observation has been pointed out by several observers, however, frequent visual observations with associated transfers from the incubator to an inverted microscope induces a physical stress that may impede or even stall embryo development. It is also time consuming and difficult to incorporate in the daily routine of IVF clinics.

Several researchers have performed time-lapse image acquisition during embryo development. This has mainly been done by placing a research microscope inside an incubator or building an "incubator stage" onto a microscope stage with automated image acquisition. The "incubator" maintain acceptable temperature (37° C.), humidity (>90%) and gas composition (5% $CO_2$ and in some cases reduced oxygen concentration). Manual assessment of time-lapse images has yielded important information about timing and duration of cell divisions (Grisart et al. 1994, Holm et al. 1998, Majerus et al. 2000, Holm et al. 2002, Holm et al. 2003, Lequarre et al. 2003, Motosugi et al. 2005).

An alternative experimental setup involves placing an image acquisition system inside an incubator to observe the embryos during development without stressing them by moving them outside the optimized conditions inside the incubator. A commercial system the EmbryoGuard is being manufactured and sold by IMT international (see literature list.) In this setup it is possible to observe the embryos online inside the incubator.

Conventional image analysis. Morphological scoring of embryo images and time-lapse videos of embryo development have relied on manual analysis where the viewer gives grades to picture and the computer only keep track of this grading, generating an annotated timeline showing when major changes occurred. An example of such software is the annotation software provided with the time-lapse image acquisition system of EmbryoGuard. Examples of manual analysis of time-lapse videos can be found in Grisart et al. 1994, Holm et al. 1998, Majerus et al. 2000, Holm et al. 2002, Holm et al. 2003, Lequarre et al. 2003, Motosugi et al. 2005.

Current software for quantitative image analysis of embryo pictures employs a semiautomatic or computer assisted algorithm. This is a computer aided image scoring where the user uses drawing tools to delineate embryonic structures that are subsequently quantified based on the user derived outline of these. Several programs to perform semiautomatic analysis of embryo pictures are commercially available (e.g. FertiMorph from ImageHouse, Copenhagen, Denmark). Several attempts have been made to make a fully automated analysis system (e.g. PhD thesis of Christina Hnida) for embryo pictures. However, the general use of Hoffmann modulation contrast (HMC) images in embryology and IVF laboratories have made automatic cell detection difficult.

Automated image analysis has been developed for other applications such as detection of mitotic cells in cell cultures (Eccles et al. 1986, Klevecz et al. 1988 U.S. Pat. No. 4,724,543, Belien et al. 1997, and Curl et al. 2004). All the reported automatic algorithms use the classical scheme for quantitative image analysis:

1. Acquire image
2. Enhance image
3. Segment image into regions of interest (ROI's) by thresholding
4. Count and characterize the ROI's (size, density etc.)

A general description of these steps and numerous variants of each can be found in review articles and textbooks on image analysis (e.g. the review of histological image analysis by Oberholzer et al. 1996 or The Image Processing Handbook, 4th Ed. 2002 by John Russ). The best methods to enhance the presentation of structures of interest depend on the image at hand (e.g. microscopy pictures) and the representation of the structure of interest (e.g. nuclei), and many different variants have been used. However, enhancement procedures are always used to facilitate segmentation of the picture in order to identify and delineate regions of interest Once these regions have been found and identified they can be characterized further with respect to area, size, intensity, position etc.

The segmentation itself is accomplished by comparing the pixel intensity (or a function derived from the pixel intensity) to a given threshold. Areas above the threshold belong to the region of interest (ROI) which is usually the object (e.g. nuclei) that must be measured. Numerous different algorithms for this segmentation are used but they always serve the same purpose i.e. a segmentation of the image.

Automated analysis of time-lapse microscopy images to detect cell division is presented in a paper by Eccles et al. 1986. The paper describes a method for automated detection of cell division in synchronized mammalian cells by analysis of images in a time-lapse series. The image analysis algorithm described and used in this paper does not use intensity differences in consecutive frames. Instead it analyses each image by first extracting high-frequency picture components, then thresholding and probing for annular objects indicative of putative mitotic cells. This operation constitutes a segmentation of the image to detect the cell outlines and their relative position. Spatial and temporal relationships between annuli on consecutive frames were examined to discern the occurrence of mitoses.

Another approach is presented in U.S. Pat. No. 23,185,450 to analyze the image sequence by using a self-similarity matrix method. The matrix consists of normalized pairwise similarity values. This method is used to analyze the long and short term similarities between frames.

All patent and non-patent references cited in the application, or in the present application, are also hereby incorporated by reference in their entirety.

SUMMARY OF THE INVENTION

The present invention relates to a method and a system for automated determination of a change in a cell population, such as a grouped cell population, such as an embryo. A change may be cellular rearrangement, such as cell movement or cell motility. Relevant changes also include cell division and cell death. The temporal pattern and magnitude of the changes indicates the quality of the cell population. Thereby the invention facilitates the selection of optimal embryos to be implanted after in vitro fertilization (IVF) or the invention may also be used to determine the number of cell divisions occurring in a confluent cell culture per time unit.

Embryo quality can be derived from the observed spatio-temporal pattern of cellular rearrangement within the zona pellucida. The amount of cellular rearrangement at a given time-point can be calculated from differences between sequentially acquired images. Many different non-normalized parameters can be used to quantify the amount of change. As described below a most preferred method is standard deviation (or variance) in the resulting difference image. As opposed to prior art it is preferred that the parameter is not normalized, i.e. that it is a measure of "difference" not similarity. One novel aspect of the invention is that temporal patterns of cellular rearrangement within an embryo can indicate embryo quality. The cellular rearrangement corresponds to movement of at least one, preferably more than two most preferably all cells within the embryo. The cellular rearrangement may be related to cell division, but have the advantage of being much more readily and easily detectable as the particular cells that undergo division need not be observed directly but can be measured indirectly by the associated rearrangement of adjacent cells. Because of the indirect effect we need not identify the dividing objects as "regions of interest" in the image (indeed the dividing cells may even be absent from the image.) Cellular rearrangement will arise as a result of cell division as the cells bump into each other and a large fraction (sometimes all) cells change position after each cell division because the embryonic cells are confined by the Zona pellucida. However, other mechanisms may cause cell movement (and cellular rearrangement) independent of cell division or may cause movement (and cellular rearrangement) to persist after cytoplasmic cell division is complete.

SUMMARY OF THE INVENTION

In particular the present invention relates to the finding that parameters derived directly from a difference image obtained by comparing at least two images of the grouped cell population correlates to a change in the grouped cell population. Thus, the present invention presents an improved method as compared to prior art methods. In prior art methods, including enhancements used to analyze sequential images such as time lapse images, a calculation of intensity difference between consecutive frames for each pixel in the image are used as starting point for subsequent employment of conventional image analysis of enhancement and segmentation before any information of the embryo or the cells is obtained.

Accordingly, in a first aspect the invention relates to a method for determining a change in a cell population comprising at least one cell, said method comprising the steps of
  a) sequentially acquiring at least two images of the cell population
  b) comparing at least a part of the at least two images obtaining at least one difference image
  c) computing a parameter from the at least one difference image, and
  d) based on said computed parameter determining whether a change has occurred.

Furthermore, in a second aspect the invention relates to a system for determining a change in a cell population comprising at least one cell, said system comprising
  a) means for sequentially acquiring at least two images of the cell population
  b) means for comparing at least a part of the at least two images obtaining at least one difference image
  c) computer for computing a parameter from the at least one difference image, and
  d) means for determining whether a change has occurred based on said computed parameter.

In a third aspect the invention relates to a method for selecting a fertilised oocyte or embryo suitable for transplantation, freeze preservation or elimination said method comprising
  a) determining changes in the oocyte or embryo by a method as defined in any of the claims, and
  b) selecting the oocyte or embryo suitable for transplantation, freeze preservation or elimination In a fourth aspect the invention relates to a system for determining the quality of a cell population comprising at least one cell, said system comprising
  a) means for sequentially acquiring at least two images of the cell population
  b) means for comparing at least a part of the at least two images obtaining at least one difference image
  c) computer for computing a parameter from the at least one difference image, and
  d) means for determining whether a change has occurred based on said computed parameter.

In a fifth aspect the invention relates to a method for determining a the quality of a cell population comprising at least one cell, said method comprising the steps of
  a) sequentially acquiring at least two images of the cell population
  b) comparing at least a part of the at least two images obtaining at least one difference image
  c) computing a parameter from the at least one difference image d) based on said computed parameter determining the quality of the cell population.

Furthermore, in a preferred embodiment the said cell population is an embryo or oocyte.

BRIEF DESCRIPTION OF THE DRAWINGS

FIG. 10 Average blastomere activity for all acquired frames (Light area=high blastomere activity, dark area=low blastomere activity).

FIG. 13 Application of selection criteria based on A) R1=ratio between average blastocyst activity in part 1 and in part 3 of the blastocyst activity pattern. B) R2=ration between standard deviation of the blastocyst activity in part 2 and in part 3 of the blasocyst activity pattern.

DETAILED DESCRIPTION OF THE INVENTION

Definitions

Figure 1:
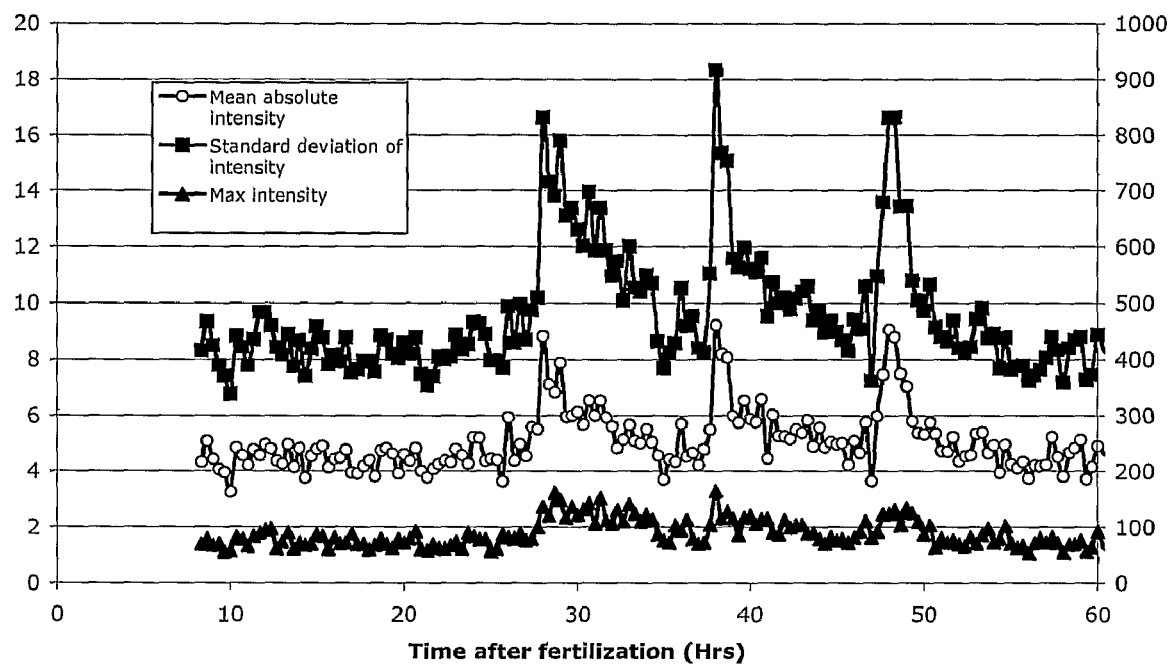
FIG. 1 Analysis of time-lapse images of bovine embryos obtained with 20 min intervals from 8 to 60 hours after fertilization. Difference images were computed as differences between consecutive frames. On the figure is shown the average absolute intensity for all pixels in the difference image (open circles), the standard deviation of the intensity (filled squares) and the maximum observed intensity (filled triangles). The latter variable is shown on the right-hand scale the others on the left hand scale. Cell division were observed after 28 hrs, 38 hrs and 48 hrs.

Cell division period: the period of time from the first observation of indentations in the cell membrane (indicating onset of cytoplasmic division) to the cytoplasmic cell division is complete so that the cytoplasm of the ensuing daughter cells are segregated in two separate cells.

Inter-division period: the period of time from end of one cell division period to the onset of the subsequent cell division period.

Division cycle: The time interval between onset of consecutive cell divisions ie. from start of one cell division period to start of the subsequent cell division Cellular movement: Movement of the center of the cell and the outer cell membrane. Internal movement of organelles within the cell is NOT cellular movement. The outer cell membrane is a dynamic structure, so the cell boundary will continually change position slightly. However, these slight fluctuations are not considered cellular movement. Cellular movement is when the center of gravity for the cell and its position with respect to other cells change as well as when cells divide. Cellular movement can be quantified by calculating the difference between two consecutive digital images of the moving cell.

Organelle movement: Movement of internal organelles and organelle membranes within the embryo which may be visible by microscopy. Organelle movement is not Cellular movement in the context of this application.

Cellular re-arrangement: A shift in position of two or more cells in the population. Cellular re-arrangement involves cellular movement of two or preferably more most preferably all blastomeres in the embryo.

Image: A transformed or un-transformed data set corresponding to a spatial distribution divided into spatial pixels (2D) or voxels (3D) recorded from the cell population. It is understood that pixels in the description of the invention pixels may be replaced by voxels without parting from the scope of the invention.

Difference image: A transformed or un-transformed data set corresponding to a spatial distribution divided into spatial pixels (2D) or voxels (3D) from the data set of two images by a pixel by pixel calculation.

Method and System for Determining Cellular Re-Arrangement

The present invention is a method and a system for determining changes in a cell population, such as a grouped cell population, such as developing embryos, by analyzing timelapse images of the grouped cell population to determine when a cell change has occurred as well as the general activity level of the cell population.

In the present context the term "grouped cell population" means a population of one or more cells, in particular a population of one or more cells wherein a cell division in the cell population leads to a 3-dimensional change in the relative position of one or more cells in the cell population. Thus, the grouped cell population is preferably a cell population growing in a lump as opposed to a cell population growing only in one or two dimensions. Examples of grouped cell populations are a developing embryo or a lump of stem cells growing on a feeder layer or a confluent cell layer where the boundaries of individual cells are difficult to discern.

Embryo

An embryo is approximately spherical and is composed of one or more cells (blastomeres) surrounded by a gelatine-like shell, a cellular matrix known as the zona pellucida. The zona pellucida performs a variety of functions until the embryo hatches, and is a good landmark for embryo evaluation. The zona is spherical and translucent, and should be clearly distinguishable from cellular debris.

An embryo is formed when an oocyte is fertilized by fusion or injection of a sperm cell (spermatozoa). The term is traditionally used also after hatching (i.e. rupture of zona pellucida) and the ensuing implantation. For humans the fertilized oocyte is traditionally called an embryo for the first 8 weeks. After that (i.e. after eight weeks and when all major organs have been formed) it is called a foetus. However the distinction between embryo and foetus is not generally well defined.

During embryonic development, blastomere numbers increase geometrically (1-2-4-8-16-etc.). Synchronous cell division is generally maintained to the 16-cell stage in embryos. After that, cell division becomes asynchronous and finally individual cells possess their own cell cycle. For bovine cells: The cells composing the embryo should be easily identified by the 16-cell stages as spherical cells. After the 32-cell stage (morula stage), embryos undergo compaction. As a result, individual cells in the embryo are difficult to evaluate beyond this stage. For human embryos compaction occurs somewhat earlier and individual balstomeres can not readily be counted at the 16 cell stage. Human embryos produced during infertility treatment are usually transferred to the recipient before the morula stage, whereas other mammalian embryos are often cultured experimentally to a further development stage (expanded blastocysts) before transfer to the recipient or discharge. In some cases also human embryos are cultivated to the blastocyst stage before transfer. This is preferably done when many good quality embryos are available or prolonged incubation is necessary to await the result of a preimplantation genetic diagnosis (PGD). Accordingly, the term embryo is used in the conventional manner to denote each of the stages fertilized oocyte, zygote, 2-cell, 4-cell, 8-cell, 16-cell, morula, blastocyst, expanded blastocyst and hatched blastocyst.

Confluent Cell Layer and Other Examples of Application of the Present Invention

The present invention may also be used to detect cell divisions in other cell cultures than developing embryos. Of particular interest are cases where individual cell boundaries are difficult to determine exactly, and classical image analysis involving segmentation and identifying cellular objects are hard to perform. These cases include investigations of cell division in culture lumps; cell divisions in or above confluent cell layers such as bilayers or tissue samples. It may also include cell divisions of cells grown atop of feeder cell layers such as stem cells, or cells grown atop of other structures that makes traditional segmentation difficult.

Acquisition of an Image

The term "image" is used to describe a representation of the region to be examined, i.e. the term image includes 1-dimensional representations, 2-dimensional representations, 3-dimensional representations as well as n-dimensional representations. Thus, the term image includes a volume of the region, a matrix of the region as well as an array of information of the region.

The image of grouped cell population may be composed of any type of images, such as photographs, photographic films, and digital images in terms of an image generated by presented on a CCD chip, CMOS chip, video camera, still camera, flat-bed scanner, drum-scanner, laser-scanner, photo multiplier, digitizer array or any other image acquisition device the like, it is however preferred that the image is digitized in order to facilitate the subsequent image comparison.

In particular the image may be phase contrast pictures, dark field images, bright field image using Köhler optics, Hoffmann modulation contrast image, interference modulation contrast image, polarization image, a fluorescence image, an infrared image, or a near-infrared image, an ultra-violet image or a combination thereof or any other type of optics that visualize the boundaries of the individual cells and or cellular organelles such as the nucleus. Usually 8-bit images (i.e. 256 different gray levels are adequate, however high resolution (12 or 16-bit) images may also be used. Color images may be converted to gray-scale images prior to analysis but can also be analysed in different color spaces or color separated as may be useful for composite fluorescence images. Furthermore, pixels may take positive as well as negative values.

However, the images in question are images of living cells so the means of producing the images should preferably not harm the cells themselves.

Thus, by the term "acquiring an image" is included both that the images may be acquired from a camera but also from a digital storage media, computer CPU, hard disc, CDROM, book, printout, traditional photograph and scanned images as well as other sources. However, in most cases images will be acquired by a digital camera.

Normally the image is acquired using a microscope, such as a digital camera mounted in a microscope or an equivalent lens system. The level of magnification and image resolution is generally not critical, as long as the embryo preferably encompass at least 25 pixels in the image, such as at least a hundred pixels in the image. In a typical application the embryo will occupy several thousand pixels. In general the highest possible contrast and magnification should be used, though the pictures may subsequently be scaled down during analysis (see below). However in cases of very high resolution pictures (>>1 million pixels) it may be necessary to scale the picture to reduce its size (See below).

Preferably the effective resolution of the said at least two images is selected so that the largest dimension of the said cell population occupies from 1 pixels to 10 mega pixels. preferably 10 pixels to 1 mega pixels, preferably 50-1000 pixels, preferably 100-1000 pixels, preferably 200-1000 pixels, preferably 500-1000 pixels, preferably 200-500 pixels.

In one embodiment the effective resolution of the said at least two images is selected so that the largest dimension of the said cell population occupies substantially 1-10 pixels, or 10-50 pixels, or 50-100 pixels, or 100-200 pixels, or 200-500 pixels, or 500-1000 pixels, or 1000 pixels-1 mega pixels, or 1-10 mega pixels, or more than 10 mega pixels.

Preferably a sequence of consecutive images is acquired from the cell population having a number of images, such as at least 2 images, such as at least 3 images, such as at least 4 images, such as at least 5 images, such as at least 6 images, such as at least 7 images, such as at least 8 images, such as at least 9 images, such as at least 10 images, such as at least 25 images, such as at least 50 images, such as at least 100 images, such as at least 200 images, such as at least 1000 images, such as at least 10000 images, such as at least 100000 images, such as at least 1 million images, such as at least 50 million images.

The time between two consecutive acquisition is preferably at most corresponding to the time period of one cell division, and on the other hand it is preferred that a minimum of images are acquired in order to facilitate processing.

Preferably the time between two consecutive acquisitions is at least 1/100 of a seconds, preferably at least 1/50 of a second, preferably at least 1/10 of a second, preferably at least 1 second, preferably at least 10 seconds, preferably at least 1 minute, preferably at least 2 minutes, preferably at least 10 minutes, preferably at least 30 minutes, such as about 30 minutes 1 hour.

Also, the time between two consecutive acquisitions is preferably at most 2 hours, such as at most 1.5 hours, such as at most 1 hour, such as at most 30 minutes, such as at most 20 minutes, such as at most 10 minutes, such as at most 5 minutes, such as at most 2 minutes, such as at most 1 minute.

Difference Image

Previous attempts to detect cell division in embryos have tried to segment the image to count the number of blastomeres (=cells) present and to determine when that number increased. This method works well for essentially planar cell cultures as described by Eccles to detected cell division in mammalian cell lines (Eccles et al. 1986). However, it becomes much more difficult to do for three dimensional embryos where multiple images from different focal planes have to be analyzed and compared to know which sections are parts of the same blastomere. It becomes practically impossible, as image segmentation most often be performed on Hoffmann modulation contrast (HMC) images that are easily interpreted by the human visual system, but are not well suited for computer based image analysis.

The present invention does not rely on segmentation of the image to identify regions of interest such as the outline of individual blastomeres. Instead the present invention estimates cellular rearrangement in the image sequence. This is obtained by at least one and preferably a series of difference images(s) from at least two images of the grouped cell population. In some embodiments the difference image might be obtained by comparing the most resent image with a linear combination or other functional relationship of previous images. At least one parameter of said difference images is evaluated to determine a change in the grouped cell population. In a preferred embodiment the difference image(s) is obtained from consecutive/subsequent images of the cell population.

The method involves computing a difference image based on acquired image frames. Any suitable difference image may be applied according to the invention, such as a difference image obtained by subtracting two images, or a difference image obtained by establishing a ratio of the two images. The difference image may be obtained from the original images as such or from any transformation image of the two images. An example of the latter is a difference image being the logarithm transformation of the ratio of pixel intensities in the two original images. (This is equivalent to an intensity difference image between logarithm transformed images). In a preferred embodiment the difference image may be an intensity difference image.

Commonly, values for corresponding pixels in the images are correlated to the light intensity encountered at the corresponding position at the times when the images were acquired. However, other value types include phase-values, such as phase contrast, or spectral characteristics such as the ratio of energy in two spectral bands, the centre of gravity in a spectral distribution or the like. Accordingly, in a different preferred embodiment the difference image is a phase difference image or a spectral difference image. Where the first may be suitable to apply the method of the present invention to images obtained by a phase-contrast microscope whereas the latter may be suitable to apply the method of the present invention to colour images and/or more advanced spatially distributed spectroscopy.

Thus, in one embodiment the difference images are obtained by subtracting intensity values for corresponding pixels in two consecutive images i.e.

$$D_n(i,j) = I_n(i,j) - I_{n-1}(i,j)$$

Where $D_n(i,j)$ is the intensity difference at position i, j at time n $I_n(i,j)$ is the intensity at position i, j at time n $I_{n-1}(i,j)$ is the intensity at position i, j at time n−1

The difference image is often displayed as an image. This requires appropriate scaling as calculated difference may be either positive or negative. However, it is not necessary for the purpose of the present invention to establish a graphic representation of the difference, since the present invention does not rely on segmentation of difference image but merely on a numerical analysis of all the values of the pixels in the difference image $D_n(x,y)$. A graphic representation depicting the difference image is not necessary. If a graphic representation is established it is advantageous to avoid round-off or scaling which may be undesired or even detrimental to the algorithm.

In another embodiment the difference image is obtained as the intensity ratio between image intensities for pixels in consecutive images. It may be advantageous, in order to reduce noise, to transform the original images and/or the ratio in one embodiment. In one embodiment the difference image is established as the logarithm to the intensity ratio (either natural logarithm or base 10) e.g.

$$Ratio_{i,j} = \text{Log}\left(\frac{I_n(i,j)}{I_{n-1}(i,j)}\right)$$

A log-ratio image computed in this way would behave very similarly to the difference image described above and may be analyzed to produce similar information regarding cell division etc by calculating any of the general parameters mentioned below.

In a preferred embodiment the said difference images are obtained from two subsequent images in a sequence of consecutive images and the collection of parameters computed from said difference images form a time series. More preferably, this time series includes a temporal pattern of cellular re-arrangement, which in conjunction with the magnitude of peaks, valleys and/or base level may be interpreted to obtain the quality, status and/or base state of the cell population.

In a preferred embodiment the said time-series is analysed using a model derived by machine learning tools, such as PCA analysis, SVD, GPCA, Support Vector Machine, n-tuple classification model, neural network, feed-forward neural network The advantage of images obtained at regular time intervals are obvious. However, it should be noted that analysis of non-regular film images are also possible. In this case a weighting may be applied to compensate for differences in time intervals between frames. Differences between images that are obtained with short time intervals are scaled up, whereas differences between images with long time intervals are scaled down. It may even be possible to acquire images with a constant difference and thus use the time interval between acquired images as indicator of cell division.

Once the difference image is obtained, then the change from one image to the next may then be described by computing a parameter, preferably a parameter from substantially all the pixels in the difference image. These parameters are calculated based on a listing of the difference values encountered in the difference image, preferably from all the difference values encountered.

Parameter

Any suitable computed parameter can be used as indicators of change, such as a parameter computed from the difference image or part hereof, where said part is determined non-adaptively, selected from the group of: Sum of absolute value for pixels in the difference image; Mean absolute value for pixels in the difference image; Median absolute value for pixels in the difference image; Sum of squared value for pixels in the difference image; Mean squared value for pixels in the difference image; Median of squared value for pixels in the difference image; Variance of value for pixels in the difference image; Standard deviation of value for pixels in the difference image; Value values for different percentiles in the histogram of the difference image; Difference Image value minimum and maximum values; and Range or variance of difference image histogram or another parameter derived from a combination of one or more of these parameters.

In a preferred embodiment, the parameter(s) is calculated without adaptive segmentation of the image in regions of interest, and regions of non-interest for every individual frame in a series. However, a sub-section of an original image may be selected non-adaptively (e.g. by cropping the original image to center on the part which contain the embryo). The subsection is preferably fixed between images of same time-lapse series of a cell population. The analyzed subsection (e.g. containing the embryo) may be compared to other reference areas of the image to calibrate the derived parameters. An example could be to compare the standard deviation of the difference image for area containing the embryo with a similarly calculated standard deviation in an empty area from the difference image.

In some embodiments the parameter is calculated from a subset of the difference image In one embodiment the parameter computed from the difference image is selected from the group of Sum of absolute value for pixels in the difference image; and Variance of value for pixels in the difference image. In some embodiments, other functions applied to the difference image might be used to calculate the parameter.

Each of these parameters is a number that will change upon a change in the grouped cell population, such as cell division, to reflect changes in cell boundary position in the investigated image series.

In a preferred embodiment said parameter is computed from the at least one difference image based on the entire difference image.

As described above, the parameter may be computed from all pixel values in the difference image, such as Mean absolute value for all pixels in the difference image
Median absolute value for all pixels in the difference image
Variance of value for all pixels in the difference image
Maximum value for all pixels in the difference image An example of computation of the parameter would be the mean of value difference squared:

$$Mean = \frac{\sum_{i=1}^{m}\sum_{j=1}^{k} D_{i,j}^2}{m \cdot k} = \frac{\sum_{i=1}^{m}\sum_{j=1}^{k} (I_n(i,j) - I_{n-1}(i,j))^2}{m \cdot k}$$

Where
k is the length of the image,
m is the width of the image

The invention relies on the observation that the cell positions are usually relatively stationary between cell divisions, except for a short time interval around each cell division, where the division of one cell into two causes considerable rearrangement of the dividing cells as well as the surrounding cells. This rearrangement is reflected in the difference image, where the changing positions of the cell boundaries (i.e. cell membranes) causes all of the above derived parameters for the difference image to rise temporarily, such as a rise in the mean absolute value or variance. Cell divisions can thus be detected by temporary change, an increase or a decrease, in mean absolute value for all pixels in the difference image or any other of the derived parameters listed above.

The invention relies in the analysis of the temporal changes in the derived parameters. Of particular interest is the onset, magnitude and duration of pronounced extremes, peaks or valleys, in the parameter values. These extremes, peaks or valleys, frequently denote cell division events and the timing and duration of these events may be used to characterize a given cell population, such as an embryo, and to evaluate its development potential. The shape of each peak may also provide additional information as may the size of the peak in general. A peak may also denote an abrupt collapse of a blastomer and concurrent cell death. However, it may be possible to separate cell division events and cell death events by the peak shape and change in base values before and after the event.

FIG. 1 shows that each cell division is marked by a pronounced peak in each of the derived variables. The cell division can thus be detected by a marked increase in each of the numerous derived variables, for example the intensity variance or standard deviation as depicted in FIG. 1.

In a preferred embodiment the said parameter is a representation of the difference between the compared images. In a first preferred embodiment the parameter is maintained un-normalized with respect to another parameter(s), derived from identical computing, from other difference images obtained from the same cell population. This allows for quantitative comparison between parameter values obtained from two one cell population and values obtained from a different cell population. In a second preferred embodiment the said parameter is not calculated as nor adjusted to a normalized value between 0 and 1. In a third preferred embodiment the computed parameter is not correlated to computation of values in a self-similarity matrix.

Thus, the present invention provides a method by which is it possible to determine cell division directly and possible to determine the exact timing of the first cellular divisions.

Shape of Change in Difference Image

As described above, the invention provides a method for determining the onset of a change in the cell population. However, in one embodiment the invention further provides a method for determining quality and/or quantity information about the change, in that the peak shape is also considered to be important. A high sharp peak should reflect a quick cell division with minimal fragmentation. Whereas broader less pronounced peaks could reflect slower divisions possibly with more fragmentation. This becomes even more important with peaks corresponding to subsequent cell divisions as a sharp second peak could indicate synchronized cell division from 2 cells to 4 cells, a broader or even bimodal peak could indicate that the divisions were asynchronous (i.e. 2 to 3 cells and then 3 to 4 cells). All in all a detailed analysis of peak position, height, width, and shape provides important information about the particular division event. In this context synchronized is understood as all cell divisions occur within a time-span of 5 hours, more preferably within 3 hours, most preferably within 1 hour.

In the above, high is regarded as greater than 2 times the standard deviation of the computed parameter, preferably greater than 3 times the standard deviation of the computed parameter most preferably greater than 5 times the standard deviation of the computed parameter. Furthermore sharp is regarded to be a peak with duration less than 3 hours, more preferably duration of less than 2 hours, most preferably with duration of 1 hours or less. Instead, a broad peak is understood to have duration of more than 3 hours, more preferably more than 5 hours most preferably with duration of more than 10 hours.

Base Level

After the peaks have been identified it is possible to evaluate the base level of activity between the peaks. The base level is understood as quasi-stable or slowly changing value. This value often defined as a value which changes by less than 10% per hour preferably less than 5% per hour most preferably less than 3% per hour. The base level for each parameter between divisions also contains useful information. Cellular metabolism is associated with movement of organelles (e.g. cycling of mitochondria in the cytoplasm). This movement is reflected in the base level of several of the above parameters. This background level gives essential information about the extent of organelle movement in the cell population, a movement that will cease upon cell death. A partial reduction in the observed organelle movement corresponding to a change in base level could thus imply problems such as decay of one or more cells. Often this change is seen as abrupt change in baseline of said computed parameter indicative of death of at least one cell. Furthermore, the said change often occurs so that the said change is a marked increase followed by an abrupt reduction of the mean value of the baseline. In this context abrupt is understood as changing within less than 5 hours, preferably less than 2 hours most preferably less than 1 hour and a marked increase is understood as a notable increase preferably by more than 5% within less than 1 hour, more preferably by more than 10% within less than 1 hour most preferably by more than 30% in less than one hour. Finally, reduction is most often a slight increase followed by a substantial reduction to m/N of the original value where N is the number of cells n the cell population and m is an integer from 0 to N−1.

In one embodiment the average absolute intensity is used as a measure of overall activity, and the base level of this parameter between peaks can be seen as an indicator of embryo development and possibly development potential.

To fully exploit the base level it may be necessary to restrict the evaluation area to the overall outline of the cell population and compare the derived values for this region with a control region outside the embryo. Thus, in order to establish the base level, it may be required to select the outline of the embryo with standard image analysis procedures as described in the literature. An example hereof includes comparison of cell movement inside the embryo to "movement" outside the embryo due Brownian motion alignment problems etc. This is mostly accomplished by delineating the embryo and comparing the difference images inside the embryo with the calculated differences in a similar area outside the embryo. Delineating the embryo may be done manually or automatically by thresholding a picture containing the sum of all absolute differences in the whole time-lapse series. The outside area may simply be chosen as the remaining pixels or (preferably) by omitting boundary pixels surrounding the embryo by inflating the embryo area prior to selecting the inverse area.

Alignment

A slight inaccuracy in the positioning system so that consecutive images in a time series are not taken at the exact same spot due to inaccurate stage movement between image acquisitions in the time series may lead to suboptimal difference images. These slight shifts in position will have an effect on the difference images as all sharply defined structures will produce a halo-and-shadow effect on the difference image even if no true movement has occurred. In one embodiment consecutive images in a time series are therefore aligned, for example using pre-existing algorithms to accomplish this in combination with the invention to improve the parameters derived. Several established algorithms to align pictures have been described (John Russ, 2002). A very simple way to align pictures is to compare the original difference image to a difference image calculated after shifting one of the original images a single pixel in a given direction. If the variance of the difference image calculated after translocation is lower than the variance of the difference image of the originals then the translocation produced an improved alignment. By systematically trying out all possible translocation directions and all relevant translocation magnitudes it is possible to obtain an aligned time series. In particular in relation to embryos, alignment may be conducted with respect to zone pellucida i.e. with the aim of reducing the variance of the area that corresponds to Zona Pellucida.

Improvement of Image Quality and Removal of Artefacts

In a further embodiment it is preferred to improve image quality and remove artefacts. Artefacts may be related to the optical and/or electronic route of acquiring the image, e.g. dirt/spots positioned on the camera lens, spots due to camera artefacts, pixel errors due to camera or CCD errors, reflections that may arise from the cell population and lead to bright areas.

Thus, artefacts is any presentation on the image, not being part of the scene of the image. Thus, artefacts may for example be one or more of the following: undesired objects projected onto the image, dispersion, diffraction and/or reflection of the optic system.

Translocations to compensate for inaccurate movement will normally shift the position of the whole image including the above mentioned fixed position artefacts. Subsequent differences will thus include a false contribution from the fixed position artefacts. It is therefore important to remove fixed position artefacts prior to translocation. Different standard techniques to remove fixed artefacts are available (se John Russ, 2002) a simple version is to obtain a defocused reference image and subtract this image of the artefacts from every picture in the series. A similar effect can be obtained by subtracting an average picture of several unrelated frames of different embryos. An average of several defocused images is optimal.

Furthermore, slight in-accuracies in stage movement that are less than a pixel are difficult to remove or compensate for by a general alignment of consecutive frames by translocation. Yet even slight (less than a pixel) translations may give a significant contribution to the difference image. Another commonly encountered problem with high quality pictures are the cell organelles such as vacuoles and mitochondria that may be partly visible and give the cells a grainy appearance. The organelle movement may contribute to such an extent to the difference image that cell division become obscure and less visible in the organelle movement noise. Both of the mentioned problems may be alleviated or even eliminated by reducing the image size (scaling down the image) or blurring/smoothing the image slightly. For example a reduction of the image size of all images in the time series so that each embryo has a diameter of 100 to 200 pixels is preferable as it tends to reduce the problems with alignment and put proper focus on cell division as opposed to organelle movement. The optimal scaling may depend on the general quality of the acquired time series. It is important that this scaling is performed after removal of fixed position artefacts and translocation compensation etc. In a preferred embodiment the said scaling or reduction of resolution is performed by a method belonging to the group: resampling, averaging, smoothing, running average, bicubic interpolation, b-spline interpolation, and simple reduction of image matrix or other methods evident to a person skilled in the art.

Many camera systems employ an auto gain function that scale image intensity dynamically between frames. This is preferably avoided. Preferably it is also avoided to compute difference pictures by subtracting consecutive images in a time series and then scale these difference images individually to use the whole intensity range so the difference image is more easily evaluated by the human eye, a computation normally employed image analysis programs. This scaling should be turned off in the preference setting of the image analysis program. If this is not possible then the quantitative analysis should use variance and standard deviation that are less affected by this artefact. A generalized scaling of all difference images calculated from a time series with the same factor is not a problem and may even be recommended to better visualize the difference images. In rare cases with uneven illumination between consecutive images in the time series it may be necessary to scale the image intensity of individual frames prior to computation of intensity differences. In these cases the quantitative analysis should use variance and standard deviation that are less affected by intensity scaling artefacts.

Culture Medium

In a preferred embodiment the acquisition of images is conducted during cultivation of the cell population, such as wherein the cell population is positioned in a culture medium. Means for culturing cell population are known in the art. An example of culturing an embryo is described in PCT application No. WO 2004/056265.

Selection or Identification of Embryos

The present invention further provides a method for selecting an embryo for transplantation, freeze preservation or elimination. The method implies that the embryo has been monitored with the method for determining a change in the embryo as described above in order to determine when cell divisions have occurred and optionally whether cell death has occurred as well as the quality of cell divisions and overall quality of embryo. It is preferred to select an embryo having substantially synchronous cell division giving rise to sharp extremas in the difference images, and more preferred to select an embryo having no cell death.

The selection or identifying method may be combined with other measurements as described below in order to evaluate the quality of the embryo. The important criteria in a morphological evaluation of embryos are: (1) shape of the embryo including number of blastomers and degree of fragmentation; (2) presence and quality of a zona pellucida; (3) size; (4) colour and texture; (5) knowledge of the age of the embryo in relation to its developmental stage, and (6) blastomere membrane integrity.

The transplantation, freeze preservation for high quality or elimination for low quality embryos may then be conducted by any suitable method known to the skilled person.

Determination of Quality

The changing positions of the cell boundaries (i.e. cell membranes) causes all of the above derived parameters for the difference image to rise temporarily, such as a rise in the mean absolute intensity or variance. Cell divisions and their duration and related cellular re-arrangement, such as cell motility, can thus be detected by temporary change, an increase or a decrease, in standard deviation for all pixels in the difference image or any other of the derived parameters computed from the difference image. In the application of the present invention to the evaluation of embryos such parameters are mainly considered to reflect "blastomere activity". This relies on the observation that the cell positions are usually relatively stationary between cell divisions, except for a short time interval around each cell division, where the division of one cell into two leads to brief but considerable rearrangement of the dividing cells as well as the surrounding cells.

Accordingly, the present invention may provide an embryo quality measure being based on one or more determinations of the embryo, such as determining the length of the at least one cell division period and/or determining the cellular movement during the inter-division period and/or determining length of time period of cellular movement during an inter-division period. This measure may be used to determine whether an embryo has sufficient quality for transplantation or freeze preservation or is below quality so it is eliminated. In a preferred embodiment, the oocyte or embryo selected for transplantation or freeze preservation is the oocyte or embryo having the highest embryo quality measure and/or the said selected oocyte or embryo selected for elimination is the oocyte or embryo having the lowest embryo quality measure.

Of particular interest is the onset, magnitude and duration of cell divisions that may be quantified as peaks or valleys, in parameter values. These extremes, peaks or valleys, frequently denote cell division events and the timing and duration of these events are used to characterize a given cell population, such as an embryo, and to evaluate its development potential. The shape of each peak also provides additional information as may the size of the peak in general. A peak may also denote an abrupt collapse of a blastomer and concurrent cell death. However, it may be possible to separate cell division events and cell death events by the peak shape and change in base values before and after the event.

Thus, the embryo quality measure comprises information of cell division time period for at least one cell division, time period of inter-division period, time period of cellular movement in inter-division period, and/or extent of cellular movement in inter-division period. In a preferred embodiment the embryo quality measure comprises information of two or more of the determinations described herein. In a more preferred embodiment the embryo quality measure comprises information of all the determinations described herein.

The embryo quality measure is based on the following observations:

a) Abrupt cell divisions where the actual division of the cytoplasm proceeds rapidly and the ensuing re-arrangement of the positions of the other blastomeres occur rapidly (e.g. sharp-blastomere activity peaks) is indicative of a high quality embryo. Prolonged cytoplasmic division and extensive rearrangement of the other blastomeres afterwards indicate a poor quality embryo (e.g. broad blastomere activity peaks). (Example 3a)

b) Very little re-arrangement of blastomere position between cell divisions indicate a high quality embryo whereas movement between visible cell divisions often indicate a poor quality embryo. (Example 3a)

c) Prolonged rearrangement of cell position between cell division (e.g. broad blastomere activity peaks) is often associated with poor embryo quality, asynchronous cell division and extensive fragmentation. (Example 3a)

d) A quiet period of very little cellular movement is observed for most mammals when the embryonic genome is activated and protein synthesis switches from maternal to embryonal transcripts. If this period has: i) Early onset, ii) very low activity (=little cellular movement=quiet) and iii) early termination then it is a strong indication of a high quality embryo. The quiet period is often delayed, and sometimes interrupted by cellular movement in poor quality embryos. (Example 3b). In this context early is understood as preferably before 30 hrs after fertilization, more preferably before 27 hours after fertilization, most preferably before 25 hours after fertilization.

e) In poor quality embryos that subsequently cease development particular and persistently immobile regions are often observed which persist and ultimately lead to developmental arrest. Such immobile regions may be associated with extensive fragmentation or blastomere death and lysis. If these regions are larger than a given percentage at a given developmental stage then the embryo has very low probability to survive. This percentage could in one instance be at least 15%, in another instance at least 35%, where these percentages are expected to be species specific. In high quality embryos the cellular motility that ensue briefly after each cytoplasmic division event is initially distributed over the entire embryo surface (i.e. all blastomeres move slightly), only after compaction in the morula stage is localized movement seen (Example 3c).

f) The amount of cellular movement in different time intervals is a good indicator of embryo quality, where the suitable time intervals are expected to be species specific. A quality related parameter can be calculated from a ratio of average movement in different time-segments and/or a ratio of standard deviations in different time-segments Embryo selection procedures can be established based on the value of these parameters. (Example 3d).

g) Very early onset of the first cell division is an indication of high embryo quality. Very late onset of first (and subsequent cell divisions) indicates low quality embryos. However, for the majority of the embryos, the exact onset of the first cell division alone does not provide a clear indication of embryo quality (Example 3d)

h) Synchronized cell division in the later stages (e.g. 2→4, 4→8) is mostly found for high quality embryos whereas asynchronous cell division is often observed for low quality embryos (e.g. 2→3→4→5→6→7→8) (Example 3a)

The following determinations lead to the highest embryo quality measure:

Short cell-division periods, wherein short is defined as less than 1 hour

Little cellular movement in inter-division periods, wherein little is defined as virtually no change in cellular position beyond the usual oscillations and organelle movements that always contribute to the difference image. Little cellular movement imply that the cellular center of gravity is stationary (movement<3 µm) and the cytoplasmic membranes are largely immotile (<3 µm).

Early onset of first cell-division period, ie. before 25 hours after fertilisation for human embryos (before 30 hours after fertilisation for bovine embryos).

Short periods of cellular movements in inter-division periods, wherein short is defined as less than 3 hours Uniform distribution of cellular movement within the embryo over time, i.e. Absence of inactive areas/zones/volumes of the embryo where cellular movement is not observed over a longer period of time (i.e. >24 hours). Such immobile zones could be due to dead or dying blastomeres and fragments, which may impede further development A neural network or other quantitative pattern recognition algorithms can be used to evaluate the complex cell motility patterns described above. Such a network may be used to find the best quality embryos for transfer in IVF treatments.

Other Measurements

A final analysis step when determining the quality of an embryo could include a comparison of the made observations with similar observations of embryos of different quality and development competence, as well as comparing parameter values for a given embryo with other quantitative measurements made on the same embryo. This may include a comparison with online measurements such as blastomer motility, respiration rate, amino acid uptake etc. A combined dataset of blastomer motility analysis, respiration rates and other quantitative parameters are likely to improve embryo selection and reliably enable embryologist to choose the best embryos for transfer.

Thus, in one embodiment the method according to the invention may be combined with other measurements in order to evaluate the embryo in question, and may be used for selection of competent embryos for transfer to the recipient.

Such other measurements may be selected from the group of respiration rate, amino acid uptake, motility analysis, blastomer motility, morphology, blastomere size, blastomere granulation, fragmentation, blastomere color, polar body orientation, nucleation, spindle formation and integrity, and numerous other qualitative measurements. The respiration measurement may be conducted as described in PCT application No. WO 2004/056265.

Data Carrier

The invention further relates to a data carrier comprising a computer program directly loadable in the memory of a digital processing device and comprising computer code portions constituting means for executing the method of the invention as described above.

The data carrier may be a magnetic or optical disk or in the shape of an electronic card of the type EEPROM or Flash, and designed to be loaded into existing digital processing means.

Example 1

Basic Program Implemented in ImageJ

The basic algorith outlined above has been implemented in image program ImageJ using the macro language of this program. ImageJ is a public domain freeware program developed by Wayne Rasband from the National Institute of Health, MD, USA. It can be freely be obtained from the website: http://rsb.info.nih.gov/ij/

Figure 2:
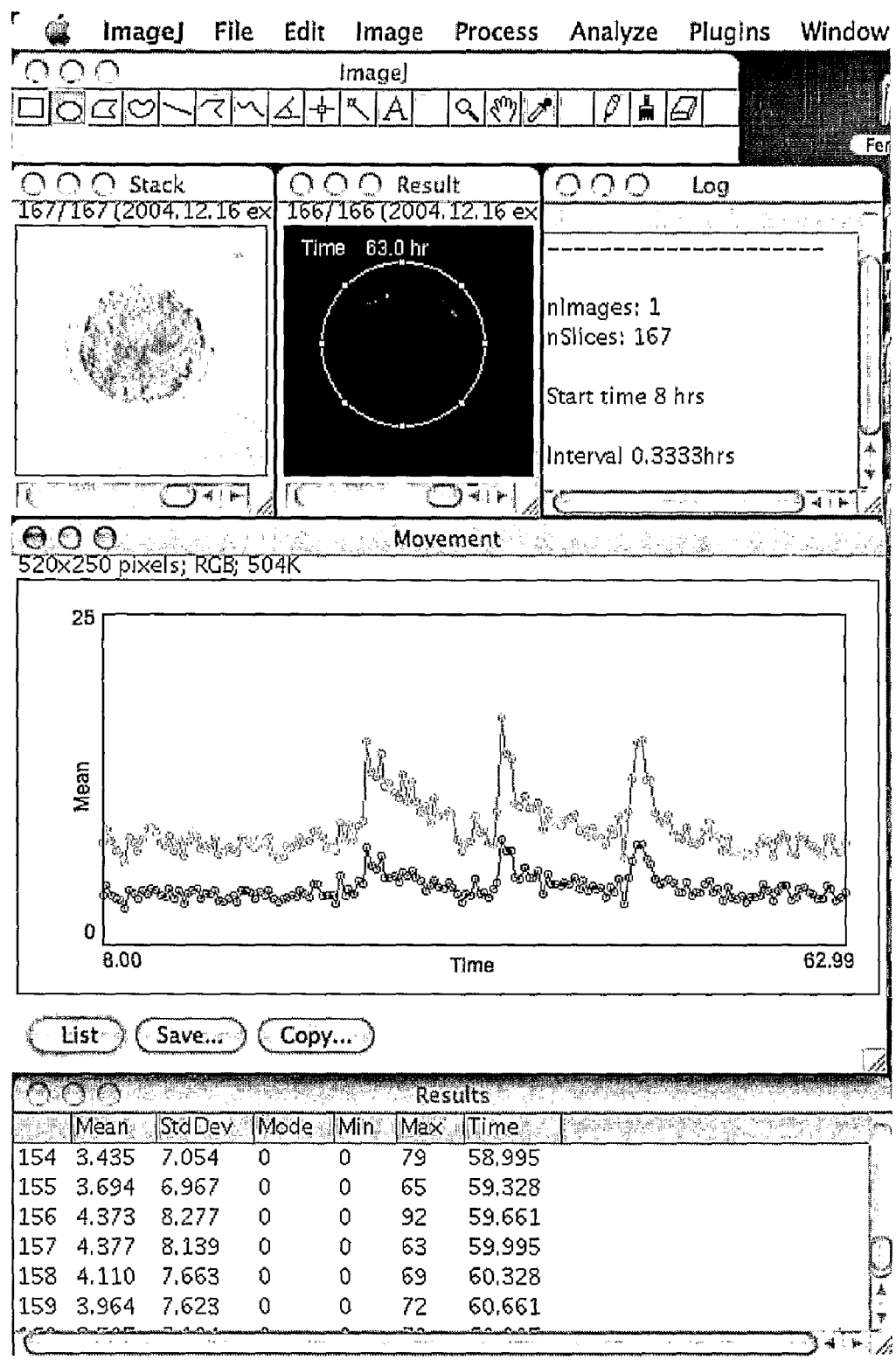
FIG. 2 Image analysis of timelapse series on bovine embryo development. Analysis of a series of 167 images obtained at 20 min intervals during embryo development. The result stack show the calculated difference images which are analyzed to produce the movement curves shown below. All analysis parameters can be exported for post processing as a tab delimited text file.

FIG. 2 is a an example of the graphical output of the program during calculations, namely a listing of the ImageJ macro source code used to analyze these images according to the invented algorithm.

```
macro "1-Open image series" {
            // Check conditions
            requires("1.33r");
            // Open image and make selection
            run("Image Sequence...");
    makeRectangle(100, 100, 150, 150);
            //print experiment parameters to log
            print("--------------------");
            print(" Experiment parameters");
            print("--------------------");
            print('');
            print('nImages: '+nImages);
            print('nSlices: '+nSlices);
}
//------------------------------------------------
macro "2-Crop" {
            // Check conditions
            requires("1.33r");
            if (nSlices==1)
                        exit("Stack required");
            if (selectionType==-1)
                        exit("Make selection first");
            doCommand('Crop');
}
//------------------------------------------------
macro "3-Difference stack" {
            // Check conditions
            requires("1.33r");
            saveSettings( );
            if (nSlices==1)
                        exit("Stack required");
            //start settings
            run("Conversions...", " ");
            //make difference stack
            run("Duplicate...", "title=Stack-copy duplicate");
            run("Delete Slice");
            setSlice(nSlices);
            run("Add Slice");
            setSlice(1);
            run("Image Calculator...", "image1=Stack
            operation=Subtract image2=
            Stack-copy create stack");
            selectWindow("Stack-copy");
            run("Close");
            //make oval selection
            selectWindow("Result");
            setTool(1);
            makeOval(30, 30, 90, 90);
            //clean up
            restoreSettings( );
}
//------------------------------------------------
macro "4-Measure movement and annotate" {
            // Check conditions
            requires("1.33r");
            saveSettings( );
            if (nSlices==1)
                        exit("Stack required");
            if (selectionType==-1)
                        exit("Make selection first");
            //print experiment parameters to log
            starttime=getNumber("Start time? (hrs)",24);
            print("");
            print("Start time " + starttime + " hrs");
            interval=getNumber("Interval? (hrs)",2);
            print("");
            print("Interval " + interval + "hrs");
            gray=getNumber("Gray? [Black=0, white=255]",255);
            //start settings
            setColor(gray, gray, gray);
            setFont("SansSerif", 12);
            min redirect=run("Set Measurements...",
            " mean standard modal min redirect=None decimal=3");
            run("Clear Results");
            //measure
            for (i=1; i<=nSlices; i++){
                        setSlice(i);
                        run("Measure");
                        integer=floor(starttime +(i-1)
                        *interval+0.01);
                        decimal=round(10*(starttime +
                        (i-1)*interval))-integer*10;
                        setJustification("left");
                        drawString("Time ",10,20);
                        setJustification("right");
                        drawString(integer + "." + decimal +
                        " hr",90,20);}
            for (i=0; i<=nSlices-1; i++){
                        setResult("Time",i,starttime + i*interval);}
            updateResults( );
            //Find variables to plot
            xValues=newArray(nSlices);
    yValues=newArray(nSlices);
    zValues=newArray(nSlices);
            for (i=0; i<nSlices; i++){
                        xValues[i] = getResult("Time",i);
                        yValues[i] = getResult("Mean", i);
                        zValues[i] = getResult("StdDev",i);}
            //Generate Plot
            Plot.create("Movement", "Time", "Mean");
            Plot.setLimits(starttime, xValues[nSlices-1], 0, 25);
            Plot.setLineWidth(1);
            Plot.setColor("red");
            Plot.add("line", xValues, yValues);
            Plot.add("circles", xValues, yValues);
            Plot.setColor("green");
            Plot.add("line", xValues, zValues);
            Plot.add("circles", xValues, zValues);
            Plot.show( );
            //save results
            selectWindow("Results");
            run("Text...");  // File>Save As>Text
            //clean up
            restoreSettings( );
}
//------------------------------------------------
macro "-" { }
//      macro "Sample Tool - C0a0L18f8L818f" {
//              getCursorLoc(x, y, z, flags);
//              print("Sample: "+x+" "+y);
//      }
//------------------------------------------------
macro "Annotate" {
            // Check conditions
            requires("1.33r");
            saveSettings( );
            if (nSlices==1)
                        exit("Stack required");
            //print experiment parameters to log
            starttime=getNumber("Start time? (hrs)",24);
            print("");
            print("Start time " + starttime + " hrs");
            interval=getNumber("Interval? (hrs)",2);
            print("");
            print("Interval " + interval + "hrs");
            gray=getNumber("Gray? [Black=0, white=255]",255);
            // start annotation
            setColor(gray, gray, gray);
            setFont("SansSerif", 12);
            for (i=1; i<=nSlices; i++){
                        setSlice(i);
```

-continued

```
            integer=floor(starttime + i*interval+0.01);
            decimal=round(10*(starttime +
            i*interval))−integer*10;
            setJustification("left");
            drawString("Time ",10,20);
            setJustification("right");
            drawString(integer + "." + decimal +
            " hr",90,20);}
     //clean up
     restoreSettings( );
)
```

Materials and methods. Bovine immature cumulus-oocyte complexes (COCs) were aspirated from slaughterhouse-derived ovaries, selected and matured for 24 h in four-well dishes (Nunc, Roskilde, Denmark). Each well contained 400 μL of bicarbonate buffered TCM-199 medium (Gibco BRL, Paisley, UK) supplemented with 15% cattle serum (CS; Danish Veterinary Institute, Frederiksberg, Denmark), 10 IU/mL eCG and 5 IU/mL hCG (Suigonan Vet; Intervet Scandinavia, Skovlunde, Denmark). The embryos were matured under mineral oil at 38.5° C. in 5% $CO_2$ in humidified air. Fertilization was performed in modified Tyrode's medium using frozen-thawed, Percoll-selected sperm. After 22 h, cumulus cells were removed by vortexing and presumptive zygotes were transferred to 400 μL of culture medium, composed of synthetic oviduct fluid medium with amino acids, citrate and inositol (SOFaaci) supplemented with antibiotics (Gentamycin sulfate, 10 mg/ml) and 5% CS and incubated at 38.5° C. in 5% $CO_2$, 5% $O_2$, 90% $N_2$ atmosphere with maximum humidity.

The incubator system has been described in detail earlier and has proved suitable for in-vitro embryo culture (Holm et al. 1998). Briefly, the 4-well culture dish was placed on the microscopic stage (MultiControl 2000 Scanning stage, Märzhäuser, Germany) of an inverted Nikon TMD microscope (Diaphot, DFA A/S, Copenhagen, Denmark). A black Plexiglas incubator box regulated by an air temperature controller (Air-Therm™, World Precision Instruments, Aston, UK) was fitted around the stage. A plastic cover with open bottom was placed over the culture dish and the humidified gas-mixture was lead into this semi-closed culture chamber after having passed through a gas washing bottle placed inside the incubator box.

This culture box has previously been proved useful for in-vitro embryo culture (Holm et al. 1998, 2003), providing stable temperature and humidity conditions. Our weekly routine in vitro embryo production during the experimental served as controls for the integrity of the basic culture system.

Camera system. The time-lapse recording was directed by an image analysis software (ImagePro™, Unit One, Birkerød, Denmark), which controlled both the movements of the scanning stage in the x-, y- and z-axes, the operation of the connected highly light sensitive video camera (WAT-902H, Watec, DFA A/S, Copenhagen, Denmark), as well as the recording and storage of time-lapse sequences on the computer hard disc.

Images of each embryo (total magnification: ×265) were sequentially recorded in minimal light at intervals of 20 min. throughout the culture period. Between recordings the embryo were moved out of the light field.

The time of the first appearance of the following cleavage/embryo stages was recorded for zygotes in focus with identifiable blastomeres: 2- and 3-4-cell stages, and for morulae and blastocysts with a visible coherent cell mass: maximal compact morula, first expansion of the blastocyst and collapses of blastocysts.

Figure 3:
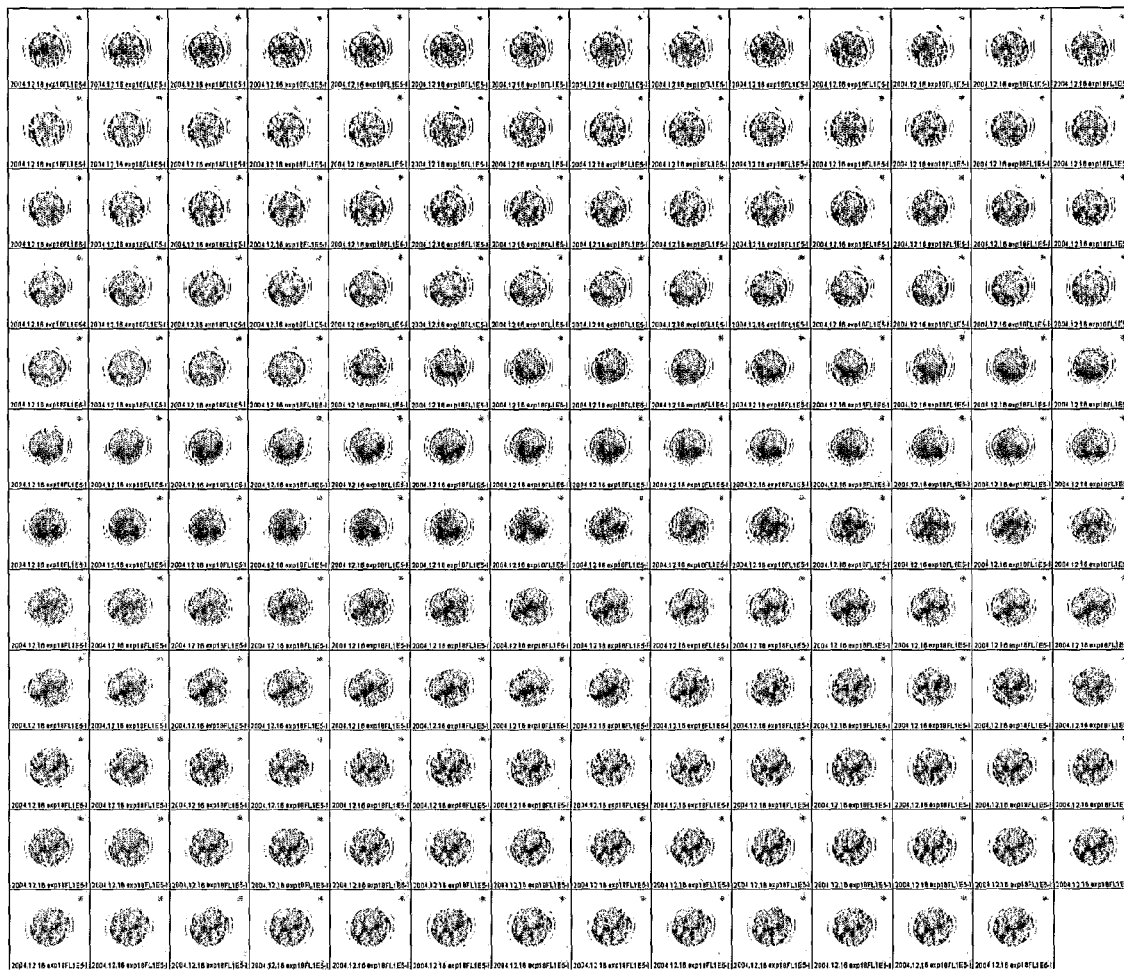
FIG. 3 Images of bovine embryo development. 167 images obtained at 20 min intervals starting 8 hours after fertilization.
Figure 4:
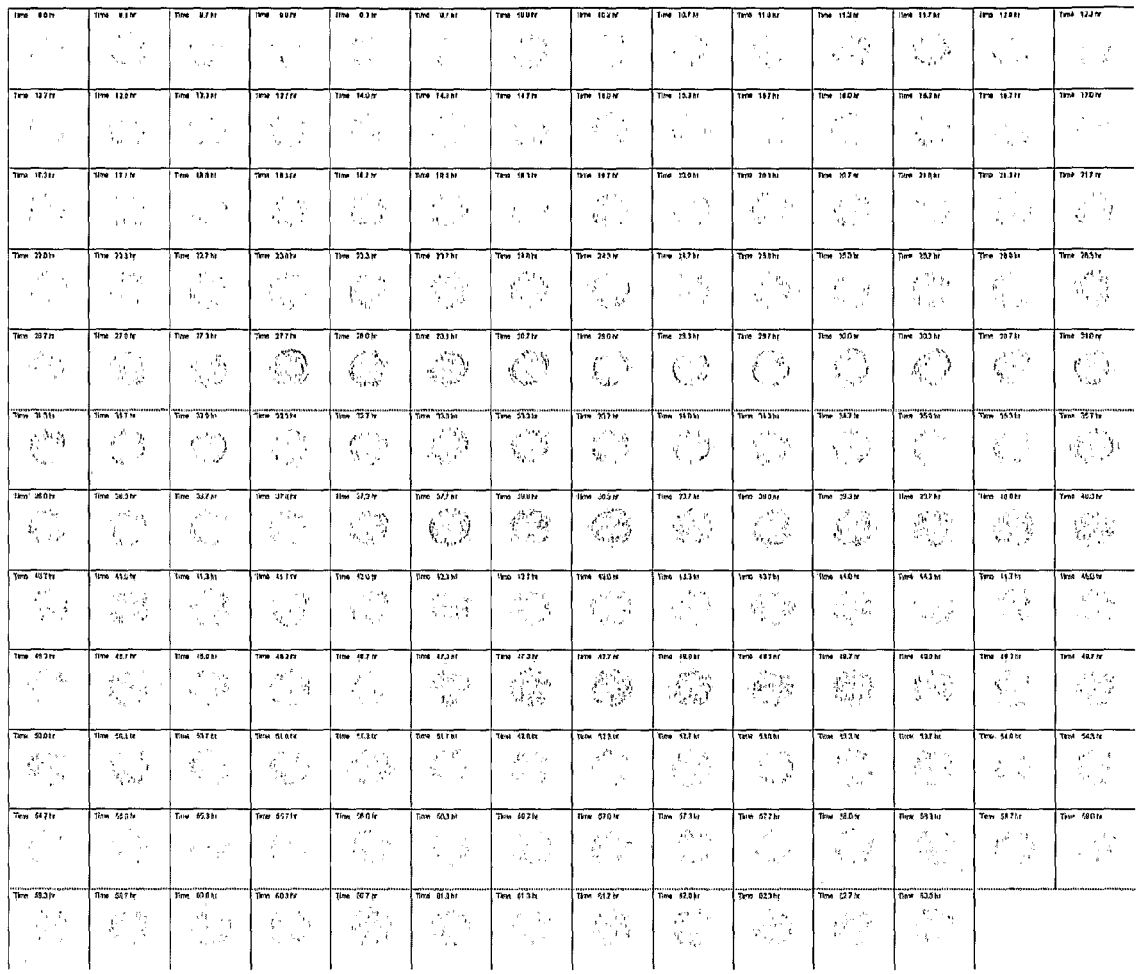
FIG. 4 Difference images calculates from the embryo images shown in FIG. 3. Acquisition time for each image as hours after fertilization is inserted.
Figure 5:
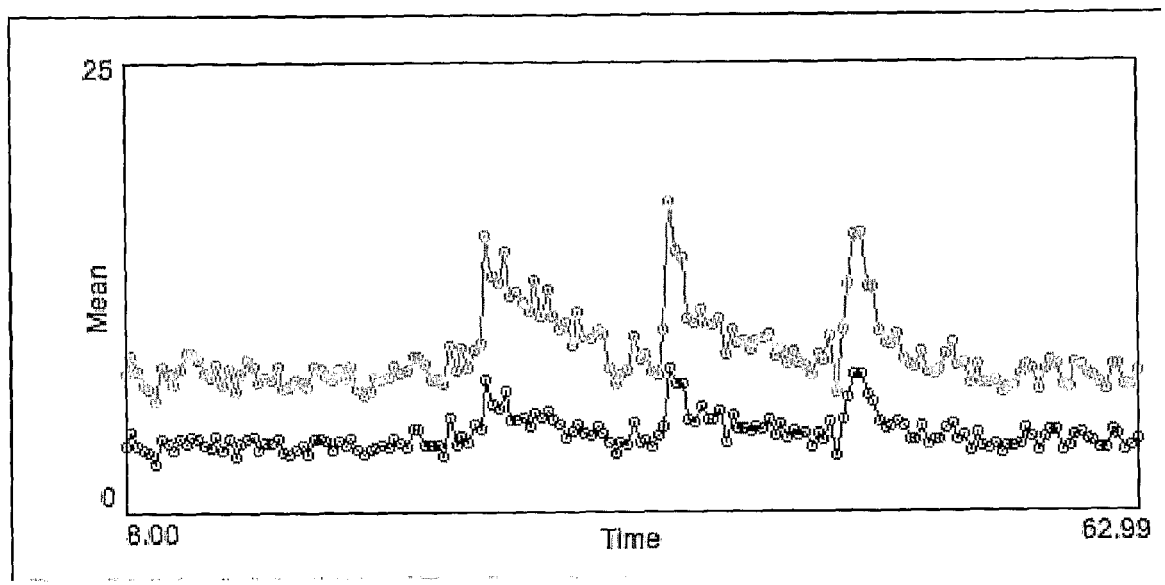
FIG. 5 Graphical output of the ImageJ macro shown in FIG. 4. Gray line is Standard deviation and Black line is mean absolute difference intensity FIG. 6 Detection of cell divisions in a confluent monolayer of cells. (e.g. stem cells growing on a layer of feeder/support cells), Direct analysis of the full area shown by open symbols in the uppermost graph. Analysis of each of the four quartiles (indicated on the photograph) are shown below. Interpretation of the full area graph is difficult whereas individual cell divisions are clearly observable in each quartile shown below. All data are theoretical used to illustrate the method principle.

FIGS. 3-5 show data series of images and analysis results as activity profile

Example 2

Theoretical Example to Quantify Cell Division in Stem Cells Growing on Monolayer of Feeder Cells The present invention may also be used to detect and quantify the number of divisions per area per time unit in a confluent cell layer (or cell divisions among stem cells growing above a confluent layer of feeder cells). The present invention is particularly useful when a poor delineation of cell boundaries, makes it unfeasible to detect, demarcate and count individual cells. However, as cell division will be associated with movement, the movement analysis of the present invention will likely reflect the cell division induced motility, provided the other cells remain stationary. Analysis of cell division in cases where individual cells can not be discerned can thus be accomplished by the method outlined in the present invention. The method will work nicely if cell divisions are rare events and thus rarely co-occurring in different parts of the image. In this case isolated peaks in the derived parameters for the whole picture will be associated with cell division. However, in many cases cell divisions will occur more frequently and some movement will always occur in different parts of the image. A simple solution is then to subdivide the image into smaller parts (e.g. 2×2, 3×3 or 4×4 etc.) so that cell division occurs relatively infrequently in each part. Use the present invention to analyse the time-series for each part separately, and then sum the results for the whole picture.

A theoretical example using hypothetical data illustrating the principle is shown in FIG. 6. In this imaginary example images of a confluent cell culture are acquired every 20 minutes for 60 hours. The time-lapse image series is analysed by calculating the difference images and computing the variance of each difference image. However, because of the relatively high number of cell divisions in the investigated area (i.e. 9) the variance of the whole picture (open symbols upper graph) is not easily interpretable. However, if the image is subdivided into four quartiles, and each quartile analyzed separately then each quartile has one to three cell divisions in the analyzed time-span, which are clearly delineated in the respective variance graph (lower figures, filled symbols). Counting the clearly defined peaks in each quartile gives the total number of cell divisions for the whole area i.e. 9 divisions in 60 hours.

The present hypothetical example illustrates an ideal situation where cell division did not occur along the boundaries of two compartments, and there were not double counting of a single division event. However, call divisions at boundaries may also be omitted if the resulting peak in both neighbouring quartiles are below threshold. It is thus unclear if edge effects will lead to an overestimate or an underestimate of real values and will clearly represent a useful approximation.

Example 3

Determining the Quality of a Cell Population

Embryo Quality Assessment

Determining the optimal embryos to be implanted after in vitro fertilization (IVF) has been found to possible based on the timing, duration and extent of observed cell divisions and associated cellular movement.

Accordingly, a first aim is to determine embryo quality by performing a method comprising monitoring the embryo for a time period using the above described method for determining change in a cell population, said time period having a length sufficient to comprise at least one cell division period and at least a part of an inter-division period, and determining the length of the at least one cell division period and/or determining the cellular movement during the inter-division period and/or determining length of time period of cellular movement during an inter-division period thereby obtaining an embryo quality measure.

The obtained embryo quality measure may then be used for identifying and selecting embryos suitable of transplantation into the uterus of a female in order to provide a pregnancy and live-born baby.

Thus, a second aim is to enable informed selection of an embryo suitable for transplantation by performing a method-comprising monitoring the embryo as defined-above obtaining an embryo quality measure, and selecting the embryo having the highest embryo quality measure.

Example 3a

Experiments, Observation, Analysis and Discussion

Materials and methods. Bovine immature cumulus-oocyte complexes (COCs) were aspirated from slaughterhouse-derived ovaries, selected and matured for 24 h in four-well dishes (Nunc, Roskilde, Denmark). Each well contained 400 µL of bicarbonate buffered TCM-199 medium (Gibco BRL, Paisley, UK) supplemented with 15% cattle serum (CS; Danish Veterinary Institute, Frederiksberg, Denmark), 10 IU/mL eCG and 5 IU/mL hCG (Suigonan Vet; Intervet Scandinavia, Skovlunde, Denmark). The embryos were matured under mineral oil at 38.5° C. in 5% $CO_2$ in humidified air. Fertilization was performed in modified Tyrode's medium using frozen-thawed, Percoll-selected sperm. After 22 h, cumulus cells were removed by vortexing and presumptive zygotes were transferred to 400 µL of culture medium, composed of synthetic oviduct fluid medium with amino acids, citrate and inositol (SOFaaci) supplemented with antibiotics (Gentamycin sulfate, 10 mg/ml) and 5% CS and incubated at 38.5° C. in 5% $CO_2$, 5% $O_2$, 90% $N_2$ atmosphere with maximum humidity.

The incubator system has been described in detail earlier and has proved suitable for in-vitro embryo culture (Holm et al. 1998). Briefly, the 4-well culture dish was placed on the microscopic stage (MultiControl 2000 Scanning stage, Märzhäuser, Germany) of an inverted Nikon TMD microscope (Diaphot, DFA A/S, Copenhagen, Denmark). A black Plexiglas incubator box regulated by an air temperature controller (Air-Therm™, World Precision Instruments, Aston, UK) was fitted around the stage. A plastic cover with open bottom was placed over the culture dish and the humidified gas-mixture was lead into this semi-closed culture chamber after having passed through a gas washing bottle placed inside the incubator box.

This culture box has previously been proved useful for in-vitro embryo culture (Holm et al. 1998, 2003), providing stable temperature and humidity conditions. Our weekly routine in vitro embryo production during the experimental served as controls for the integrity of the basic culture system.

Camera system. The time-lapse recording was directed by an image analysis software (ImagePro™, Unit One, Birkerød, Denmark), which controlled both the movements of the scanning stage in the x-, y- and z-axes, the operation of the connected highly light sensitive video camera (WAT-902H, Watec, DFA A/S, Copenhagen, Denmark), as well as the recording and storage of time-lapse sequences on the computer hard disc.

Time-lapse Images of each embryo (total magnification: ×265) were sequentially recorded in minimal light at intervals of 30 min. throughout the 7 day culture period. Between recordings the embryo were moved out of the light field.

Manual analysis of the time-lapse image series consisted of recording the time of the first appearance of the following cleavage/embryo stages: 2-cell, 4-cell, 8-cell, 16-cell and for moru-lae and blastocysts with a visible coherent cell mass: maximal compact morula, first expansion of the blastocyst, collapses of blastocysts and hatching of the blastocyst.

The automated computer based analysis consisted of computing the standard deviation of the differences image which is calculated as the difference between two consecutive frames. To avoid alignment artifacts and other problems the following elaborate procedure was used:

1) Image acquisition. (See description above).

2) Remove fixed position artifacts (Camera dust) by subtracting a defocused reference image of the artifacts from every picture in the series.

3) Translocation to compensate for inaccurate stage movement. A very simple way to align pictures is to compare the original difference image to a difference image calculated after shifting one of the original images a single pixel in a given direction. If the variance of the difference image calculated after translocation is lower than the variance of the difference image of the originals then the translocation produced an improved alignment. By systematically trying out all possible translocation directions and all relevant translocation magnitudes it is possible to obtain an aligned time series. However in the present case we used an advanced ImageJ macro for image alignment developed by Thévenaz et al. 1998.

4) Identify region of interest (ROI) and reference area outside. It is advantageous to compare cell movement inside the embryo to "movement" outside the embryo due Brownian motion alignment problems etc. This is accomplished by delineating the embryo and comparing the difference images inside the embryo with the calculated differences in a similar area outside the embryo. Delineating the embryo was done manually. A reference area we chose a region of the image without any embryos.

5) Calculate intensity difference.

6) Compute a derived parameters for each difference image. Several difference parameters were calculated but the one that proved most informative was the standard deviation of intensity for all pixels in the difference image. This parameter is referred to as the "blasomere activity" in the following, as well as in the following examples.

7) Identify and determine shape of peaks in the blastomere activity.

8) Calculate standard deviation and average values for the blastomere activity for diagnostically relevant time intervals See example 3d.

Experimental design. Approx. 20 bovine embryos were incubated together in a single well of a Nunc-4well dish for 7 days with image acquisition every 30 min. This experiment was repeated 5 times total giving time-lapse image series of 99 bovine embryos.

Results:

Based on qualitative evaluation of time-lapse image series of developing embryos, (essentially by looking playing them as movies numerous times and noting changes), we observed that: An indicator of high quality embryos is abrupt cell divisions where the actual division of the cytoplasm proceeds rapidly and the ensuing re-arrangement of the positions of the other blastomeres occur rapidly followed by a period of "quiet" with very little rearrangement of cell position until the abrupt onset of the next cytoplasmic division. Poor quality embryos often show prolonged rearrangements of blastomere position after cytoplasmic divisions and between cytoplasmic cell divisions. To quantify and document these observations we calculate blastomere activity from a time-lapse image series.

Figure 7:
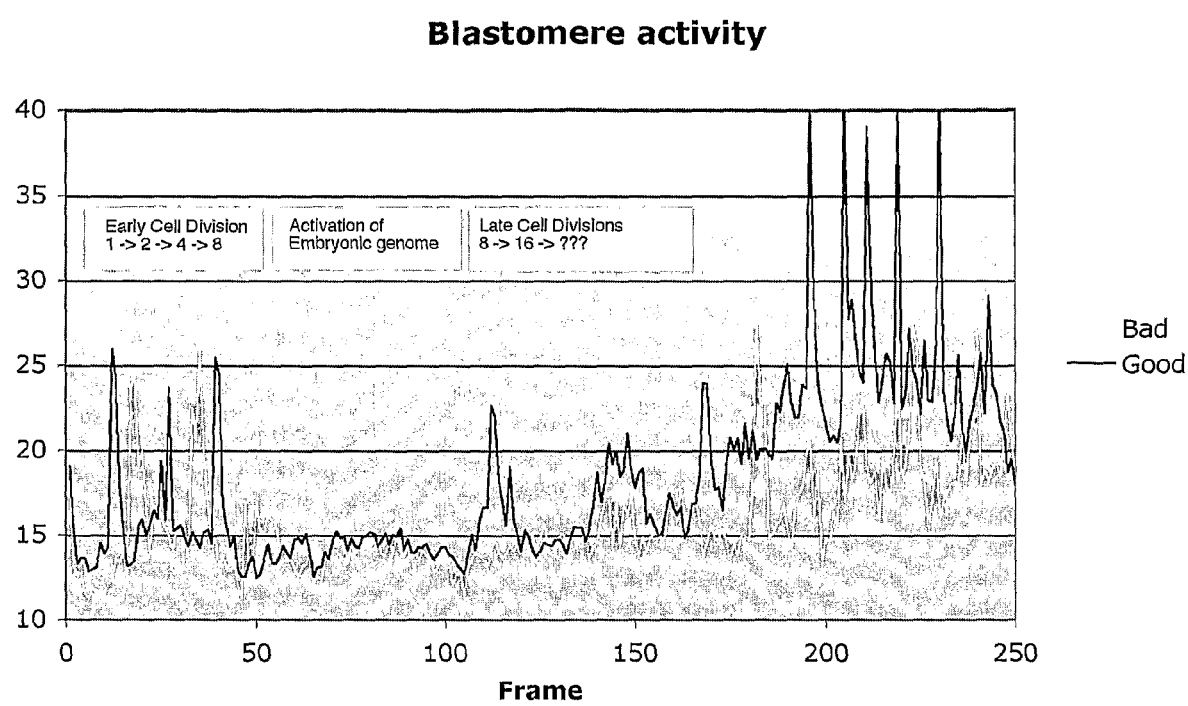
FIG. 7 Blastomere activity of two representative bovine embryos. "Good" developed to a hatching bastocyst, whereas "Bad" never developed to blastocyst.

Representative blastomere activities are shown in the FIG. 7 for a "good" and a "bad" embryo, respectively. The embryo considered "Good" developed to a hatching bastocyst, whereas the embryo considered "Bad" never developed to a blastocyst.

Figure 8:
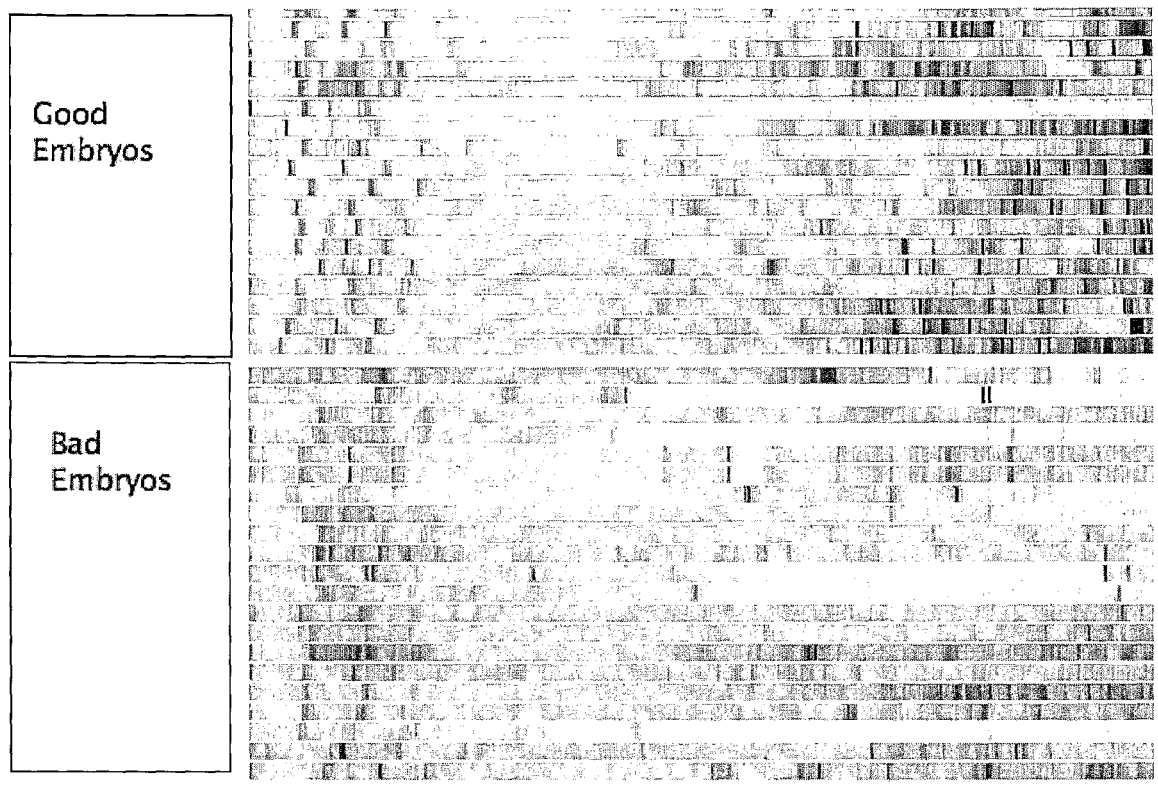
FIG. 8 Blastomere activity of 41 bovine embryos from 24 to 175 hours after fertilization. The blastomere activity is displayed as a pseudo-gel-image where motility peaks are indicated by dark bands and inactivity is white each lane corresponds to a single embryo and each pixel correspond to the difference obtained within 30 minutes.

Some of the observed activity is due to asynchrous cell division (e.g. 2→3→4→5→6→7→8) and fragmentation as opposed to synchronous cell divisions (e.g. 2→4, 4→8) observed for high quality embryos. In FIG. 8 The blastomere activity of 41 embryos is displayed as a pseudo-gel-image where motility peaks are indicated by dark bands and inactivity is white, each lane corresponds to a single embryo. The dark banding pattern or smears reflect periods of cellular motility within the embryo. "Good" embryos developing to blastocysts shown above "bad" embryos that did not develop to the blastocyst stage. More sharp initial bands (usually three) are seen for good embryos Example 3b Experiments, Observation, Analysis and Discussion Materials and Methods. Same as for Example 3a
Results
Initial protein synthesis in mammalian embryos use maternal mRNA from the oocyte, but after a few cell divisions the embryonic genome is activated, transcribed and translated. The switch from maternal genome to embryonic genome is a crucial step in embryo development. The period occurs at the 8-cell stage for bovines and has a relatively long duration for human embryos the switch occurs earlier at the 4 to 8 cell stage and has a shorter duration.

Figure 9:
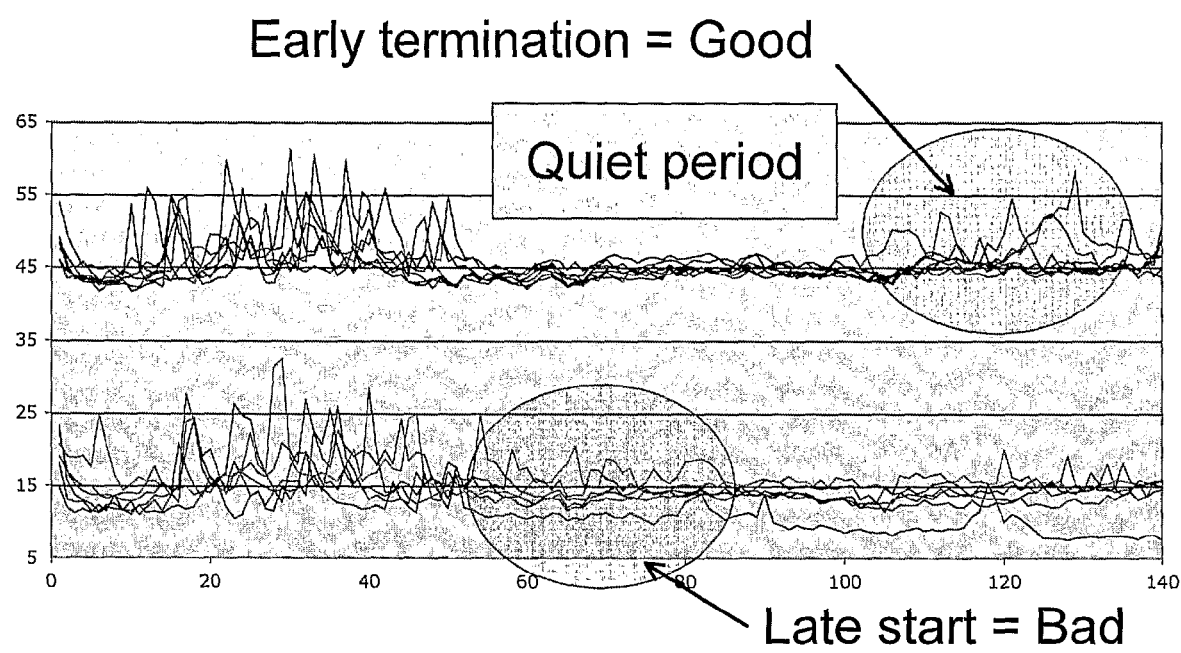
FIG. 9 Blastomere activity of thirteen representative bovine embryos. "Good" embryos developed to a hatching bastocyst are represented by green curves. "Bad" embryos never developed to blastocyst are shown in read. X-axis is frame number y-axis is blastomere activity. Image acquisition started 24 hours after fertilization and progressed with 2 frames per hour. The green curves have been displaced on the y-axis by adding 30 to the blastomere activity value.

A quiet period of very little cellular movement is observed for most mammals when the embryonic genome is activated and protein synthesis switches from maternal to embryonal genes. If this period has: i) Early onset, ii) very low activity (=little cellular movement=quiet) and iii) early termination then it is a strong indication of a high quality embryo. The quiet period is often delayed, and sometimes interrupted by cellular movement in poor quality embryos. An example of this showing blastomere activity, defined in example 3a, for 13 different embryos are shown in FIG. 9. The dark banding pattern or smears reflect periods of cellular motility within the embryo. "Good" embryos developing to blastocysts shown above "bad" embryos that did not develop to the blastocyst stage. More sharp initial bands (usually three) are seen for good embryos.

Example 3c

Experiments, Observation, Analysis and Discussion

Materials and Methods. Same as for Example 3a
Results
In poor quality embryos that subsequently cease development particular and persistently immobile regions are often observed which persist and ultimately lead to developmental arrest. Such immobile regions may be associated with extensive fragmentation or blastomere death and lysis. If these regions are larger than a given percentage at a given developmental stage then the embryo has very low probability to survive. In high quality embryos the cellular motility that ensue briefly after each cytoplasmic division event is initially distributed over the entire embryo surface (i.e. all blastomeres move slightly), only after compaction in the morula stage is localized movement seen Embryos that develop to blastocysts such as the left panel in FIG. 10 have uniformly distributed blastomere activity (defined in example 3a). Embryos that do not have uniformly distributed blastomere activity such as the right panel in FIG. 10 never develops into a blastocyst.

Example 3d

Experiments, Observation, Analysis and Discussion

Figure 11:
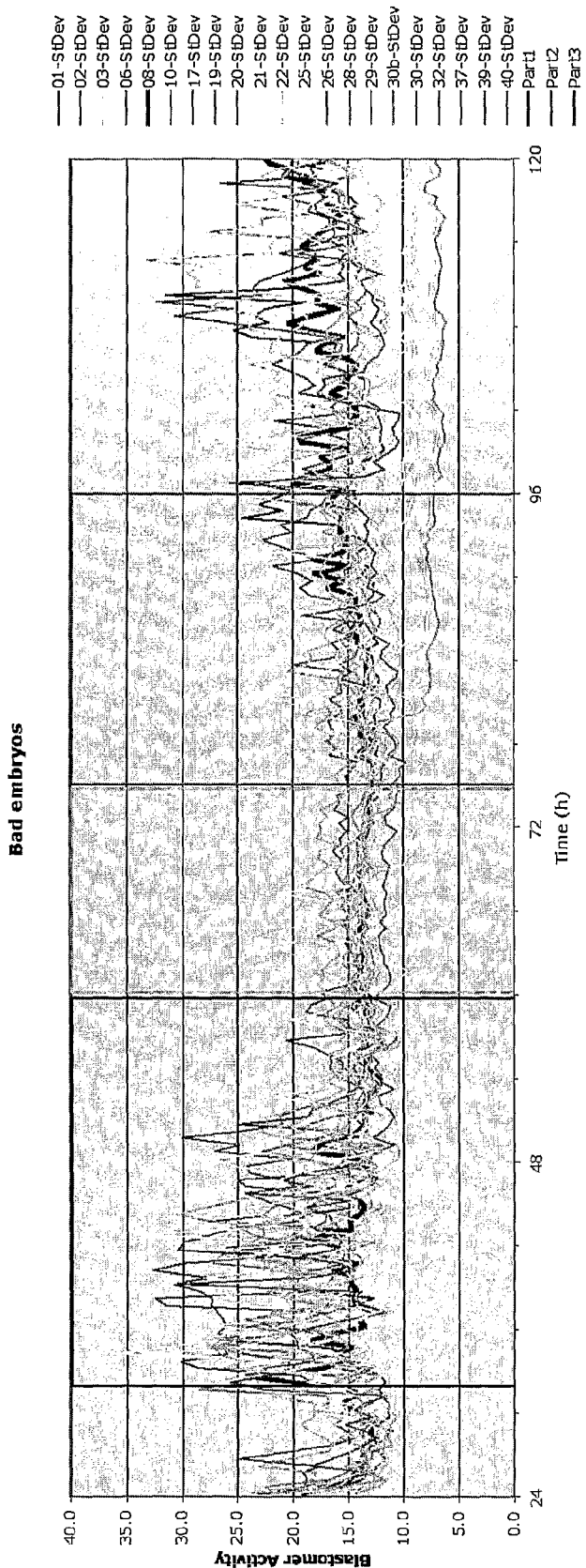
FIG. 11 Blastomere activity of 21 bovine embryos that did not develop to high quality blastocysts. The three parts of the curves that are used to classify the blastomere activity pattern are indicated.
Figure 12:
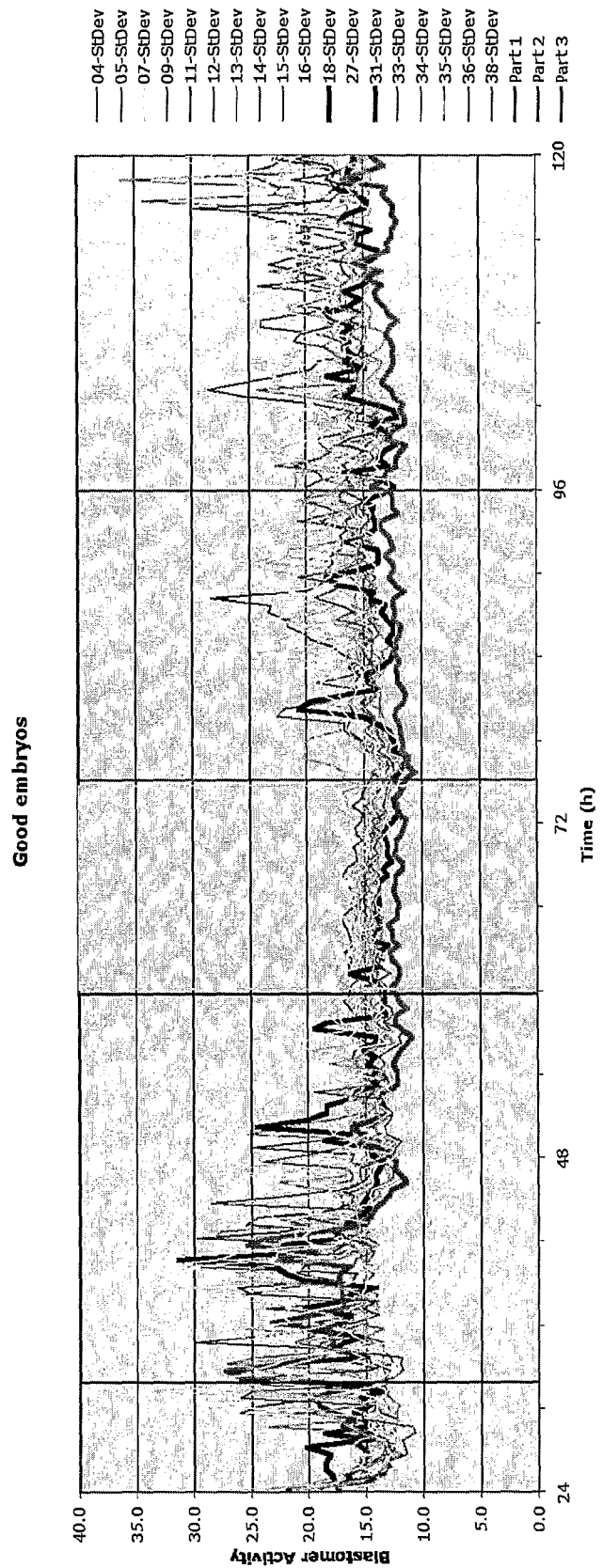
FIG. 12 Blastomere activity of 18 bovine embryos that did not develop to high quality blastocysts. The three parts of the curves that are used to classify the blastomere activity pattern are indicated.

Materials and Methods. Same as for Example 3a
Results
The amount of cellular movement in different time intervals is a good indicator of embryo quality. A quality related parameter can be calculated from a ratio of average movement in different time-segments and/or a ratio of standard deviations in different time-segments Embryo selection procedures can be established based on the value of these parameters. Example of different segments (=parts) are in FIGS. 11 and 12. In this case is part 1 the time segment from 32 to 60 hours after fertilization, part 2 is 60 to 75 hours after fertilization, part 3 is from 75 to 96 hours after fertilization.

Based on the average blastomer activity and/or the standard deviation of the blastomere activity (defined in example 3a) in the different parts it is possible to classify the embryos.

In the present case we have used the following selection criteria based on:
R1=ratio between average blastocyst activity in part 1 and in part 3 of the blastocyst activity pattern for a given embryo
R2=ration between standard deviation of the blastocyst activity in part 2 and in part 3 of the blastocyst activity pattern for a given embryo
The calculations are shown in FIG. 13.
If (R1<1.15 and R2<0.50) then it is a "good" embryo ELSE it is a "bad" embryo. Using these criteria all 36 out of 39 embryos were classified correctly according to how they subsequently developed.

Example 3e

Experiments, Observation, Analysis and Discussion

Figure 14:
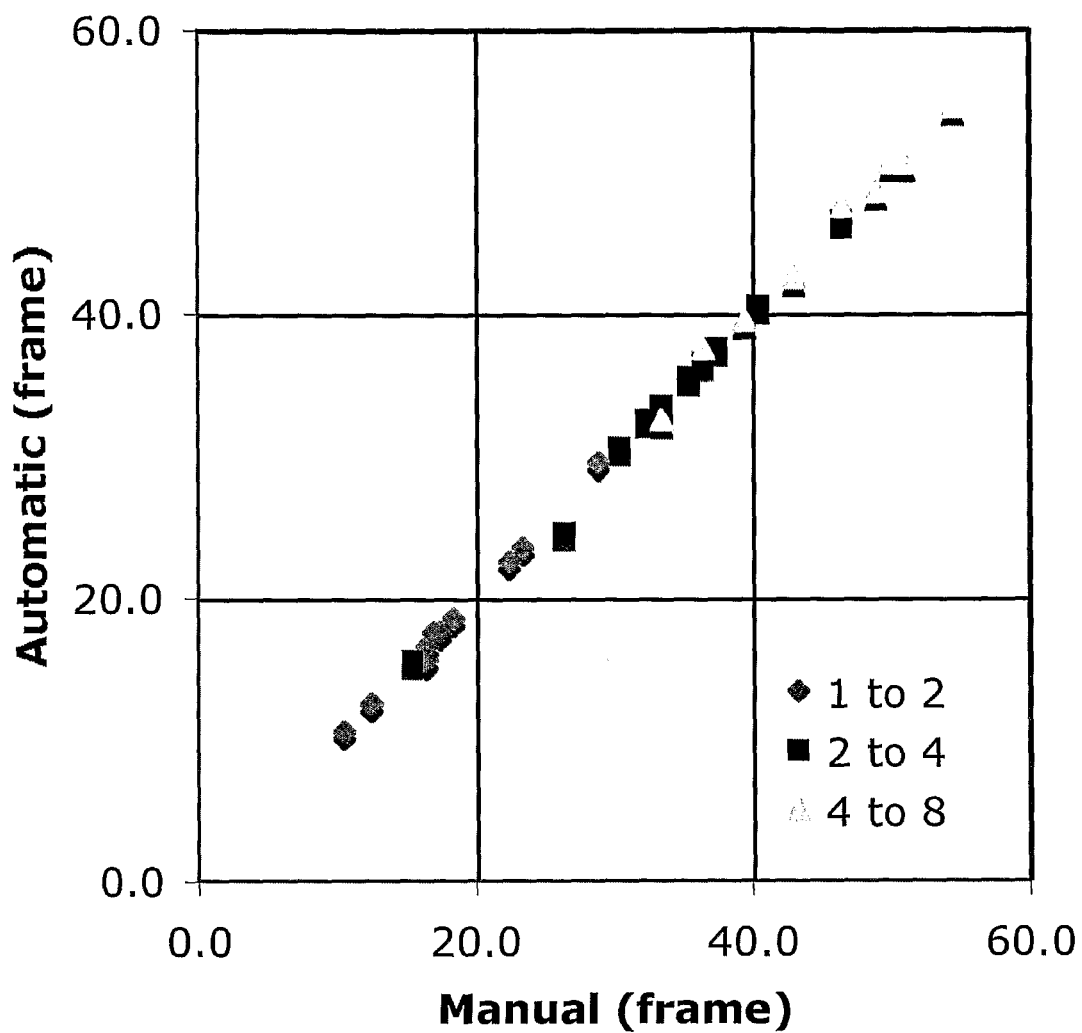
FIG. 14 Correlation between cell divisions detected manually and automatically for 13 representative embryos. About 10% of the cell divisions were not detected by this algorithm, but otherwise the correspondence is excellent.

Materials and Methods. Same as for Example 3a
Results
FIG. 14 show the excellent correspondence between automatic and manual determination of onset of cell division.

Figure 15:
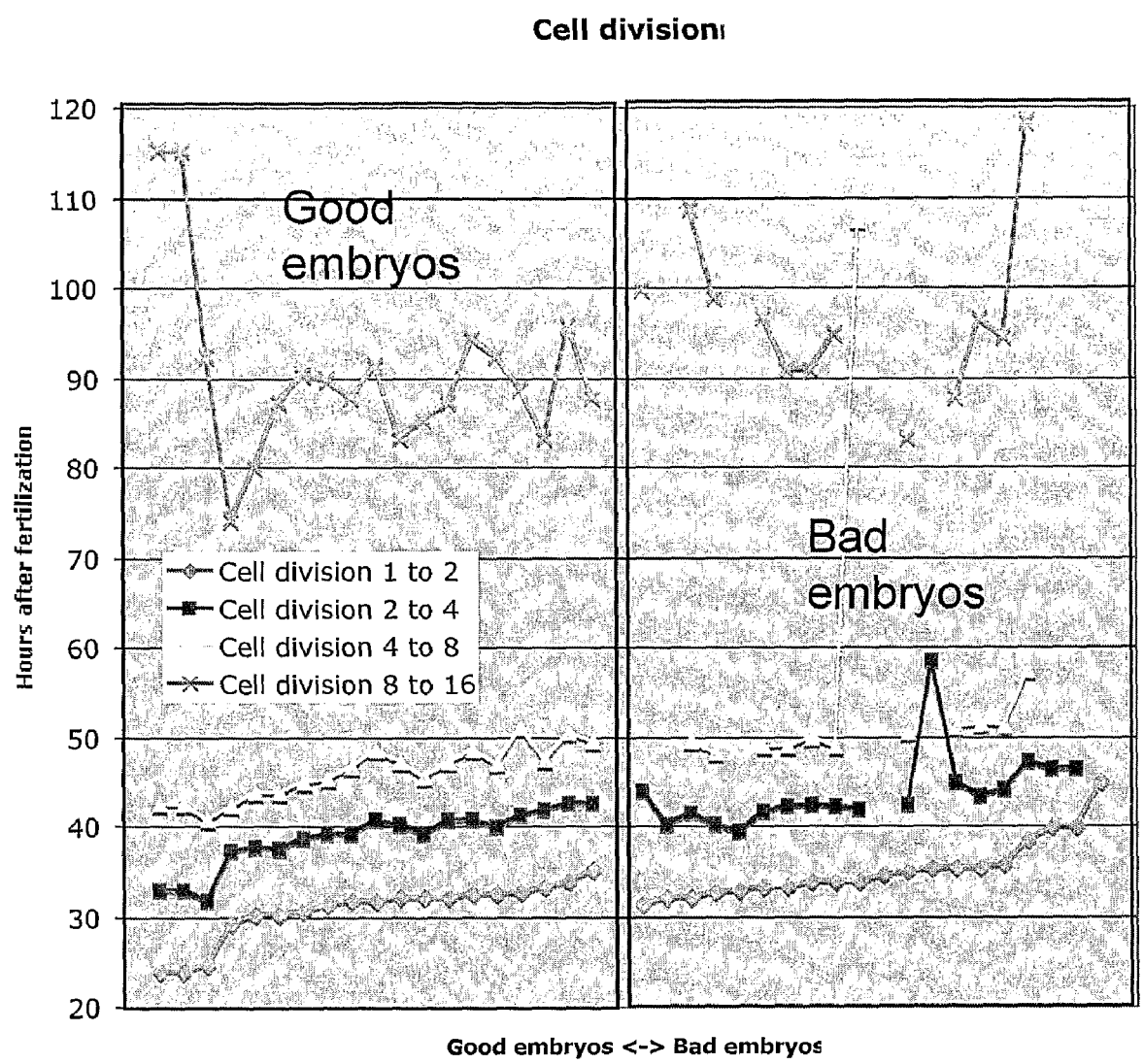
FIG. 15 Manually detected cell divisions for good and bad embryos.

Very early onset of the first cell division is an indication of high embryo quality. Very late onset of first (and subsequent cell divisions) indicates low quality embryos. However, for the majority of the embryos, the exact onset of the first cell division alone does not provide a clear indication of embryo quality as is shown in FIG. 15.

While the average onset of cell divisions were delayed for the bad embryos, the large inherent standard deviation makes the absolute values a poor selection criteria except in extreme cases. (e.g. first division before 30 hours signifies a good embryo. First division after 35 hours signifies a bad embryo but the vast majority of the bovine embryos investigated have intermediate division times that are not easily interpreted.

LITERATURE

Articles

Beliën J A M, Baak J P A, Van Diest P J and Van Ginkel A H M (1997) *Counting mitoses by image processing in feulgen stained breast cancer sections: The influence of resolution.* Cytometry 28: 135-140

Bhattacharya S and Templeton A (2004). *What is the most relevant standard of success in assisted reproduction? Redefining success in the context of elective single embryo transfer: evidence, intuition and financial reality.* Human reproduction page 1-4

Bos-Mikich A, Mattos A L G and Ferrari A N (2001) *Early cleavage of human embryos: an effective method for predicting successful IVF/ICSI outcome.* Hum Reprod 16, 2658-2661.

Curl C L, Harris T, Harris P J, Allman B E, Bellair C J, Stewart A G and Delbridge L M D (2004) *Quantitative phase microscopy: a new tool for measurement of cell culture growth and confluency in situ.* Pflugers Arch-Eur J Physiol 448: 462-468

Eccles B A and Klevecz R R (1986) *Automatic digital image analysis for identification of mitotic cells in synchronous mammalian cell cultures.* Pubmed, anal quant cytol histol 8: 138-47

Fenwick J, Platteau P, Mucdoch A P and Herbert M (2002) *Time from insemination to first cleavage predicts developmental competence of human preimplantation embryos in vitro.* Hum reprod 17, 407-412

Grisart B, Massip a and Dessy F (1994) *Cinematographic analysis of bovine embryo development in serum-free oviduct-conditioned medium.* Pubmed, J. Reprod fertile 101 (2): 257-64

Haney S. M, Thompson P M, Cloughesy T F, Alger J R and Toga A W (2001) *Tracking tumor growth rates in Patients with Malignant gliomas: A test of two algorithms.* AJNR An J Neuroradiol 22:73-82

Christina Hnida (2004) *Computer-assisted, multilevel, morphometric analysis of bio-markers of embryonic quality.* PhD thesis, University of Copenhagen Holm P, Booth P J and Callesen H (2002) *Kinetics of early in vitro development of bovine in vivo-and in vitro-derived zygotes produced and/or cultured in chemically defined or serum-containing media.* Reproduction 123: 553-565

Holm P, Booth P J and Callesen H (2003) *Developmental kinetics of bovine nuclear transfer and parthenogenetic embryos.* Cloning and stem cell Vol 5 number 2

Holm P, Shukri N N, Vajta G, Booth P, Bendixen C and Callesen H (1998) *Developmental kinetics of the first cell cycles of bovine in vitro produced embryos in relation to their in vitro viability and sex.* Theriogenology 50: 1285-1299

Lundin K, Bergh C and Harderson T (2001) *Early embryo cleavage is a strong indicator of embryo quality in human IVF.* Hum Reprod 16, 2652-2657

Majerus V, Lequarre A S, Ferguson E M, Kaidi S, Massip A, Dessy F and Donnay I (2000) *Characterization of embryos derived from calf oocytes: Kinetics of cleavage, cell allocation to Inner cell mass, and trophectoderm and lipid metabolism.* Molecular reproduction and development 57: 346-352

Motosugi N, Bauer T, Polanski Zbigniew, Solter D and Hiiragi T (2005) *Polarity of the mouse embryo is established at blastocyst and is not prepatterned.* Genes & development 19: 1081-1092

Oberholzer M, Ostreicher M, Christen H and Bruhlmann M (1996) *Methods in quantitative image analysis.* Pubmed, histochem cell boil 105: 333-55

Petersen C G, Mauri A L, Ferreira R, Baruffi R L R and Franco Jr J G (2001). *Embryo selection by the first cleavage parameter between 25 and 27 hours after ICSI.* J Assist Reprod Genet 18, 209-212

Sakkas D, Percival G, D'arcy Y, Sharif K and Afnan M (2001) *Assessment of early cleaving in vitro fertilized human embryos at the 2-cell stage before transfer improves embryo selection.* Fertil Steril 76, 1150-1156

Sakkas D, Shoukir Y, Chardonnens D, Bianchi P G and Campana A (1998) *Early cleavage of human embryos to the two-cell stage after intracytoplasmic sperm injection as an indicator of embryo viability.* Hum Reprod 13, 182-187

Salumets A, Hydén-Granskog C, Suikkari A-M, Tiitinen A and Tuuri T (2002) *The predictive value of pronuclear morphology of zygotes in the assessment of human embryo quality.* Hum Reprod 16, 2177-2181

Shoukir Y, Campana A, Farley T and Sakkas D (1997) *Early cleavage of in-vitro fertilized embryos to the 2-cell stage: a novel indicator of embryo quality and viability.* Hum Reprod 12, 1531-1536

Vayena E, Rowe P J and Griffin P D (2001) *Current practices and controversies in assisted reproduction*: Report of a meeting on "Medical, Ethical and Social aspects of assisted reproduction" held at WHO headquarters in Geneva, Switzerland.

Windt M-L, Krueger T F, Coetzee K and Lombard C J (2004) *Comparative analysis of pregnancy rates after the transfer of early dividing embryos versus slower dividing embryos.* Hum Reprod Vol 19 No 5 pp 1155-1162

Books

John C Russ (2002) *The Image Processing Handbook*, CRC press, 4'th Edition ISBN: 084931142X Patents Bongiovanni Kevin Paul, Audi Paul Patrick, Fortin Christophers, McPhillips Kenneth (Feb. 24, 2005) *Automatic target detection and motion analysis form image data.* US2005041102

Cecchi Michael D, Mezezi Monica (Jul. 24, 2003) *Biological specimen-culturing system and method with onboard specimen development sensors.* US2003138942

Garankani Arman M., Hack, Andrew A., Roberts Peter, Walter, Sean (Feb. 13, 2003) *Method and apparatus for acquisition, compression, and characterization of spatiotemporal signals.* US20030185450

Iwasaki Masahiro, Imagawa Taro (Apr. 28, 2005) *Monitoring device.* WO02005039181

Myers James Carrol (Jun. 25, 2004) *A method of searching recorded digital video for areas of activity* MXA03003268, U.S. Pat. No. 6,434,320 (B1)

Klevecz Robert R., Eccles Beverly A. (Feb. 9, 1988) *Method and apparatus for automatic digital image analysis.* U.S. Pat. No. 4,724,543

Tago Akira, Tsujii Osamu (May 18, 2005) *Radiographic image processing method and apparatus*, EP1531422

Products

EmbryoGuard: Microscopic Time-Lapse and quality assurance. A product sold by IMT international, Chester, England. (http://www.cryo-imt.com/embryoguard.htm)

FertiMorph. Embryo morphology analysis software. Quantitative embryo morphology measurements and scoring using 3D stacks of images recorded at different positions in the embryo. A product sold by Image House Medical, Copenhagen, Denmark (http://www.ihmedical.com/products.aspx?id=fmorph-po)

The invention claimed is:

1. A method for determining a magnitude of a change in a cell population comprising at least one cell, said method comprising the steps of
   a) sequentially acquiring at least two images of the cell population
   b) comparing at least a part of the at least two images, thereby obtaining at least one difference image
   c) computing a parameter from the at least one difference image, wherein said parameter provides information of the magnitude of a change, and
   d) based on said computed parameter determining the magnitude of the change,
      wherein the parameter computed from the difference image is selected from the group of Sum of absolute values for pixels in the difference image; Mean absolute value for pixels in the difference image; Median absolute value for pixels in the difference image; Sum of squared values; Mean squared value for pixels in the difference image; Median of squared value for pixels in the difference image; Variance of values for pixels in the difference image; Standard deviation of values for pixels in the difference image; Values for different percentiles in the histogram of the image; Difference Image minimum and maximum values; and Range or variance of histogram or another parameter derived from a combination of one or more of these parameters.

2. The method according to claim 1, wherein the said parameter is computed from the at least one difference image based on the entire difference image.

3. The method according to claim 1, wherein the said parameter is calculated without adaptive segmentation of the image in regions of interest, and regions of non-interest.

4. The method according to claim 1, wherein the cell population is an embryo.

5. The method according to claim 1, wherein the change in the cell population is cellular re-arrangement.

6. The method according to claim 1, wherein the change in the cell population is cell division.

7. The method according to claim 1, wherein the change in the cell population is death of at least one cell.

8. The method according to claim 1, wherein the difference image is obtained by subtracting values for corresponding pixels in the at least two images.

9. The method according to claim 1, wherein the difference image is obtained by computing the ratio of values for corresponding pixels in the at least two images.

10. The method according to claim 1, wherein the difference image is an intensity difference image.

11. The method according to claim 1, wherein the values corresponding to pixels in the difference image is difference in intensity.

12. The method according to claim 1, wherein the values corresponding to pixels in the difference image is difference in spectral characteristic.

13. The method according to claim 1, wherein the said at least two images are subjected to identical scaling before said comparison to obtain at least one difference image.

14. The method according to claim 1, wherein a plurality of difference images are obtained from a sequence of consecutive images and a change in said computed parameter is indicative of a change in the cell population.

15. The method according to claim 14, wherein each of the said difference images are obtained from two subsequent images and the collection of parameters computed from said difference images form a time series.

16. The method according to claim 14 wherein an extreme in said computed parameter is indicative of cellular rearrangement.

17. The method according to claim 16, wherein an extreme in said computed parameter is indicative of cell division.

18. The method according to claim 17, wherein the shape of said extreme indicates the nature of the change occurring in the cell population.

19. The method according to claim 18, wherein a high sharp peak indicates a quick cell division with minimal fragmentation.

20. The method according to claim 18, wherein a broad and/or bimodal peak indicates slower cell divisions and/or more fragmentation.

21. The method according to claim 18, wherein a broad and/or bimodal peak indicates asynchronous cell division.

22. The method according to claim 1, wherein the determination of a change in the grouped cell population is compared to other measurements of the grouped cell population.

23. A method for determining a the quality of a cell population comprising at least one cell, said method comprising the steps of
   e) sequentially acquiring at least two images of the cell population:
   f) comparing at least a part of the at least two images, thereby obtaining at least one difference image
   g) computing a parameter from the at least one difference image; wherein said parameter provides information of the magnitude of a change, and
   h) based on said computed parameter determining file quality of the cell population,
      wherein the determining embryo quality comprising monitoring the embryo for a time period, said time period having a length sufficient to comprise at least one cell division period and at least a part of an inter-division period, and determining the length of the at least one cell division period and/or determining the cellular movement during the inter-division period and/or determining length of time period of cellular movement during an inter-division period thereby obtaining an embryo quality measure.

24. The method according to claim 23 further comprising any of the features of claim 1.

25. The method according to claim 23, wherein the embryo is monitored for a time period comprising at least two cell division periods.

26. The method according to claim 23 for determining embryo quality comprising monitoring the embryo for a time period, said time period having a length sufficient to comprise at least one period of cellular rearrangement and a period without substantial cellular rearrangement and using the method described in claim 1 to determine the temporal distribution of cellular rearrangement thereby obtaining an embryo quality measure.

27. The method according to claim 26, wherein the embryo is monitored for a time period comprising at least two cell division periods.

28. The method according to claim 23, wherein the length of time for each rearrangement period and/or cell division period is determined.

29. The method according to claim 23, wherein the length of time between each rearrangement period and/or cell division period is determined.

30. The method according to claim 23, wherein the period of cellular movement in at least two inter-division periods is determined.

31. The method according to claim 23, wherein the extent of cellular movement is as determined in at least two inter-division periods is determined.

32. The method according to claim 23, wherein determination of the length of the at least one cell division period and determination of cellular movement during the inter-division period are performed.

33. The method according to claim 23, wherein short duration of cellular rearrangements following cell division is indicative of a high quality embryo.

34. The method according to claim 33, wherein the duration of the cellular rearrangement is determined by the method described in claim 1.

35. The method according to claim 23, wherein a high sharp parameter peak determined by the method described in claim 1 is indicative of a high quality embryo.

36. The method according to claim 23, wherein prolonged cytoplasmic division and extensive and/or prolonged re-arrangement of the other blastomeres afterwards indicate a poor quality embryo.

37. The method according to claim 36, wherein the said extensive and/or prolonged re-arrangement of the other blastomeres is indicated by a broad peak in the blastomere activity.

38. The method according claim 23, wherein persistently immobile regions in an embryo indicates a poor quality embryo.

39. The method according to claim 23, wherein the absence of immobile regions without movement before compaction in the morula stage indicates a high quality embryo.

40. The method according to claim 23, wherein the ratio of average movement in suitable time-segments and/or a ratio of standard deviations for the difference image in different time-segments is a quality parameter.

41. The method according to claim 40, wherein the said time-segments for a bovine embryo are substantially 32-60 hours after fertilization and/or 60-75 hours after fertilization and/or 75-90 hours after fertilization.

42. The method according to claim 23, wherein cell division periods of less than substantially 1 hour raise the embryo quality measure.

43. The method according to claim 23, wherein little cellular movement in inter-division periods raise the embryo quality measure.

44. The method according to claim 23, wherein early onset of first cell-division period, i.e. before 25 hours after fertilisation for human embryos raise the embryo quality measure.

45. The method according to claim 23, wherein uniform distribution of cellular rearrangement such as cellular movement within the embryo over time raise the embryo quality measure.

46. A method for selecting a fertilised oocyte or embryo suitable for transplantation, freeze preservation or elimination said method comprising
    a) determining changes in the oocyte or embryo by a method as defined in claim 23, and
    b) selecting the oocyte or embryo suitable for transplantation, freeze preservation or elimination.

47. The method according to claim 46, wherein the said selected oocyte or embryo is the oocyte or embryo having the highest embryo quality measure.

48. The method according to claim 46, wherein the said selected oocyte or embryo is the oocyte or embryo having the lowest embryo quality measure.

49. The method according to claim 46, wherein the said selected oocyte or embryo is the oocyte or embryo having a particular attributes comprising a particular temporal pattern in one of the parameters determined by the methods in claim 1.

* * * * *